United States Patent [19]

Damon

[11] Patent Number: 5,429,500
[45] Date of Patent: * Jul. 4, 1995

[54] SELF-LOCKING ORTHODONTIC BRACKET

[75] Inventor: Dwight H. Damon, Spokane, Wash.

[73] Assignee: Damon Family Limited Partnership, Spokane, Wash.

[*] Notice: The portion of the term of this patent subsequent to Jan. 4, 2011 has been disclaimed.

[21] Appl. No.: 140,690

[22] Filed: Oct. 20, 1993

Related U.S. Application Data

[63] Continuation-in-part of Ser. No. 45,529, Apr. 28, 1993, Pat. No. 5,275,557.

[51] Int. Cl.$^6$ .............................................. A61C 3/00
[52] U.S. Cl. ...................................... 433/10; 433/13; 433/14
[58] Field of Search ..................... 433/8, 9, 10, 11, 13, 433/14, 3, 17, 24

[56] References Cited

U.S. PATENT DOCUMENTS

| | | | |
|---|---|---|---|
| 1,280,628 | 10/1918 | Angle | 433/14 |
| 1,821,171 | 9/1931 | Atkinson | 433/14 |
| 2,230,315 | 2/1941 | Winslow | 433/11 |
| 2,671,964 | 3/1954 | Russell et al. | 433/13 |
| 3,091,857 | 6/1963 | Rubin et al. | 433/11 |
| 3,128,552 | 4/1964 | Broussard | 433/13 |
| 3,131,474 | 5/1964 | Johnson | 433/11 |
| 3,497,954 | 3/1970 | Kesling | 433/13 |
| 3,835,539 | 9/1974 | Wallshein | 433/14 |
| 4,015,334 | 4/1977 | Moss | 433/17 |
| 4,023,274 | 11/1977 | Wallshein | 433/11 |
| 4,103,423 | 8/1978 | Kessel | 433/10 |
| 4,144,642 | 3/1979 | Wallshein | 433/11 |
| 4,180,912 | 1/1980 | Kesling | 433/13 |
| 4,197,642 | 4/1980 | Wallshein | 433/11 |
| 4,209,906 | 7/1980 | Fujita | 433/11 |
| 4,242,085 | 12/1980 | Wallshein | 433/14 |
| 4,248,588 | 2/1981 | Hanson | 433/11 |
| 4,260,375 | 4/1981 | Wallshein | 433/11 |
| 4,355,975 | 10/1982 | Fujita | 433/11 |
| 4,386,909 | 6/1983 | Hanson | 433/20 |
| 4,415,330 | 11/1983 | Daisley et al. | 433/8 |
| 4,419,078 | 12/1983 | Pletcher | 433/11 |
| 4,492,573 | 1/1984 | Hanson | 433/11 |
| 4,561,844 | 12/1985 | Bates | 433/10 |
| 4,583,944 | 4/1986 | Hanson | 433/22 |
| 4,698,017 | 10/1987 | Hanson | 433/11 |
| 4,712,999 | 12/1987 | Rosenberg | 433/11 |
| 4,838,787 | 6/1989 | Lerner | 433/14 |
| 4,850,865 | 7/1989 | Napolitano | 433/8 |
| 4,859,179 | 8/1989 | Kesling | 433/8 |
| 5,018,259 | 5/1991 | Wildman | 433/8 |
| 5,094,614 | 3/1992 | Wildman | 433/14 |
| 5,123,838 | 6/1992 | Cannon | 433/14 |
| 5,154,607 | 10/1992 | Hanson | 433/8 |
| 5,174,753 | 12/1992 | Wool | 433/20 |
| 5,254,002 | 10/1993 | Reher et al. | 433/8 |
| 5,275,557 | 1/1994 | Damon | 433/10 |

Primary Examiner—Cary E. O'Connor
Attorney, Agent, or Firm—Wells, St. John, Roberts, Gregory & Matkin

[57] ABSTRACT

A self-locking orthodontic bracket includes a base for attachment to a tooth or tooth band. Transversely spaced tying lugs project from the base and include opposed extensions for orthodontic attachment purposes. The tying lugs present an anterior surface interrupted by an archwire slot. A closure mounted on the bracket includes a movable cover slidably engaging the anterior surface of the bracket. The cover spans the full width of the tying lugs and has a perpendicular width greater than the width of the archwire slot across the anterior surface. The closure is supported on the bracket by a pair of guides that slidably engage opposed side surfaces of the tying lugs for opening and closing the cover. The closure can also be designed to complement the archwire slot structure between the lugs, forming a complete tube encircling the archwire across the full width of the bracket when the cover is in its closed position. The bracket lugs, including the closure, can also be arranged obliquely across a base to provide a tipping angle across the bracket. Bracket placement is facilitated by an encircling shield or cap, including protruding extensions to aid in aligning and locating the bracket on a supporting tooth surface.

43 Claims, 16 Drawing Sheets

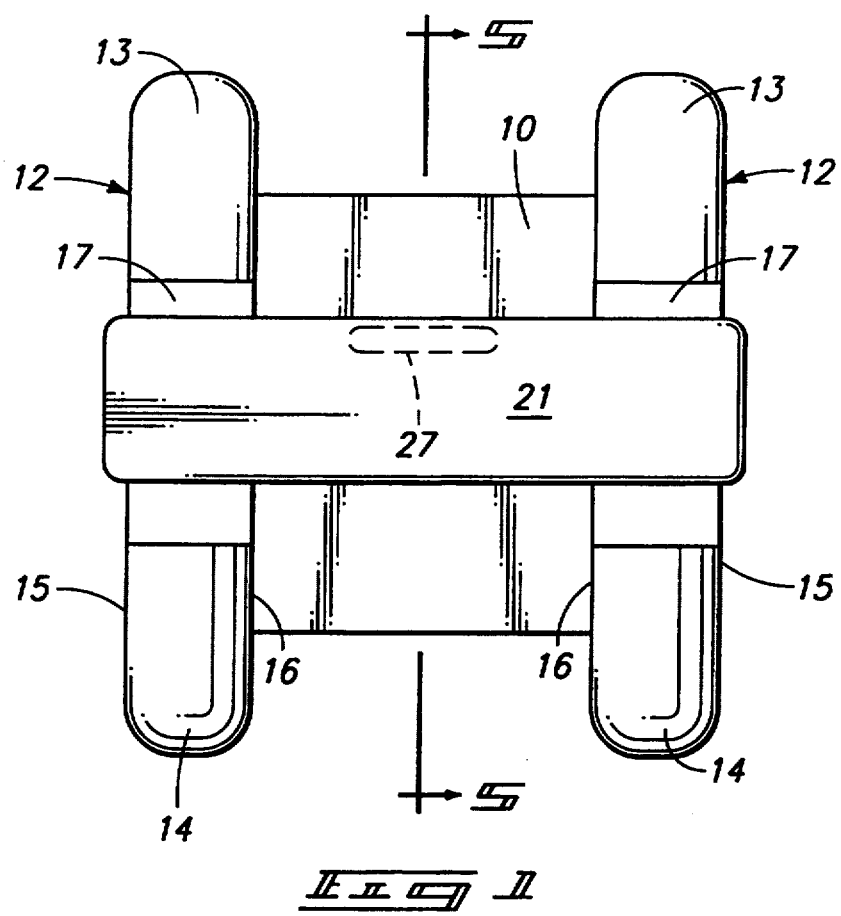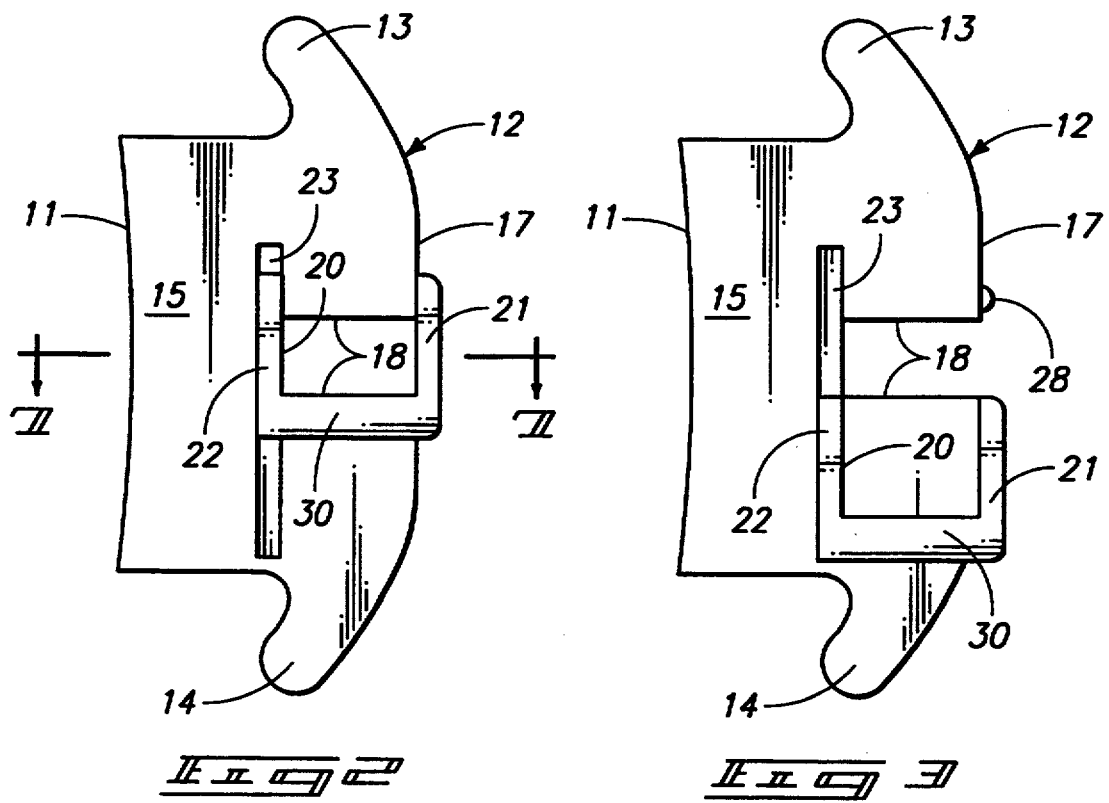

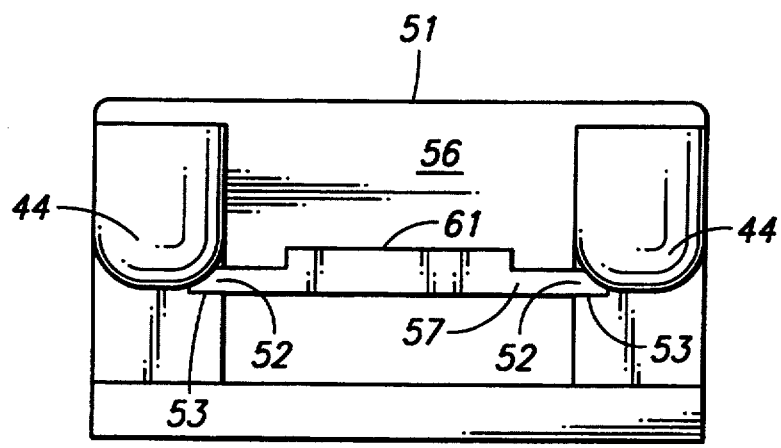
_Fig 12_
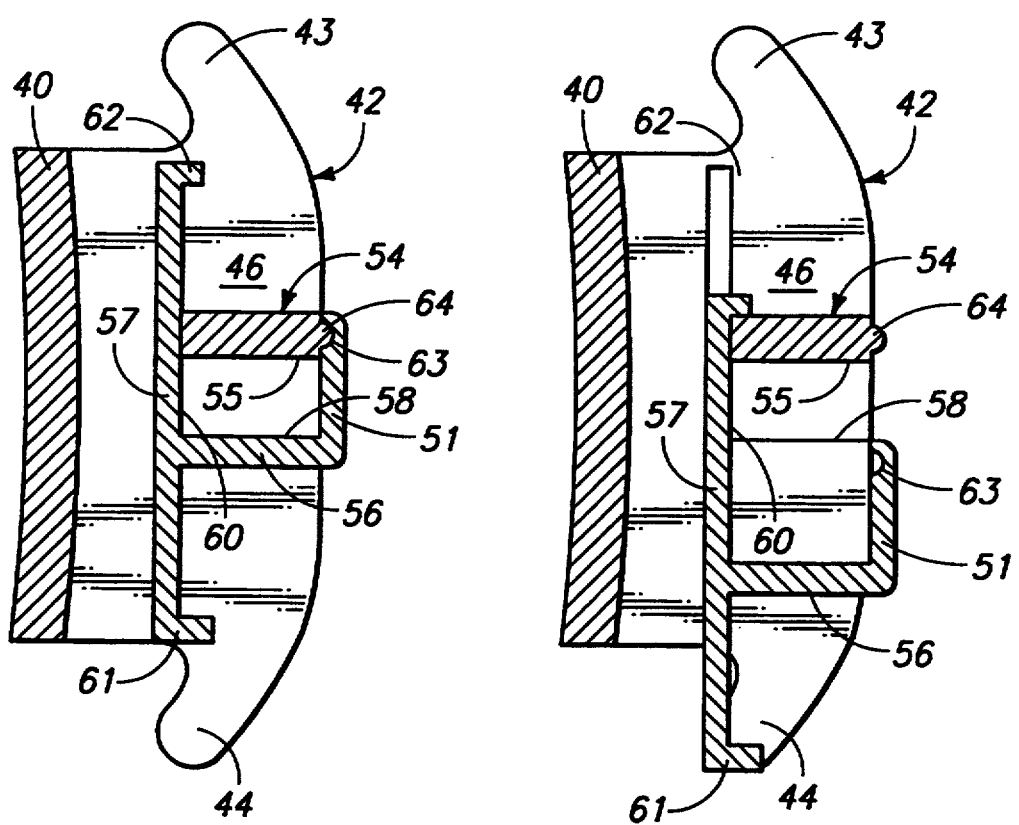
_Fig 13_  _Fig 14_

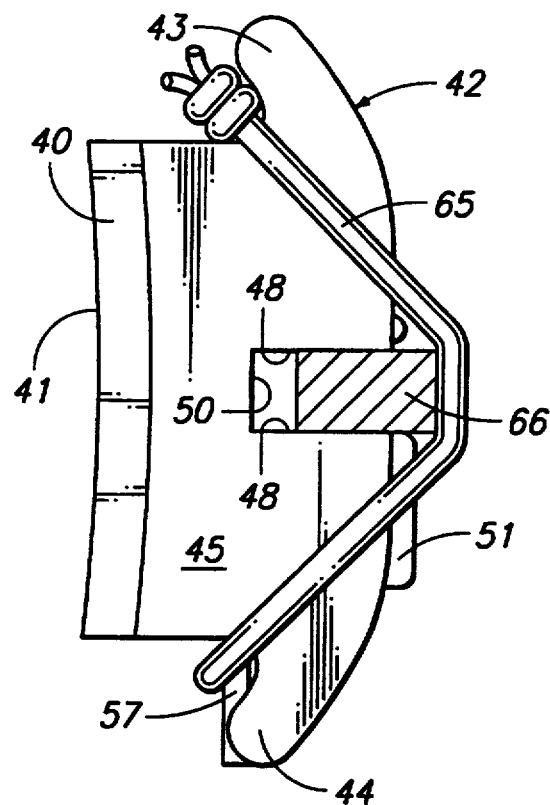
_Fig 15_
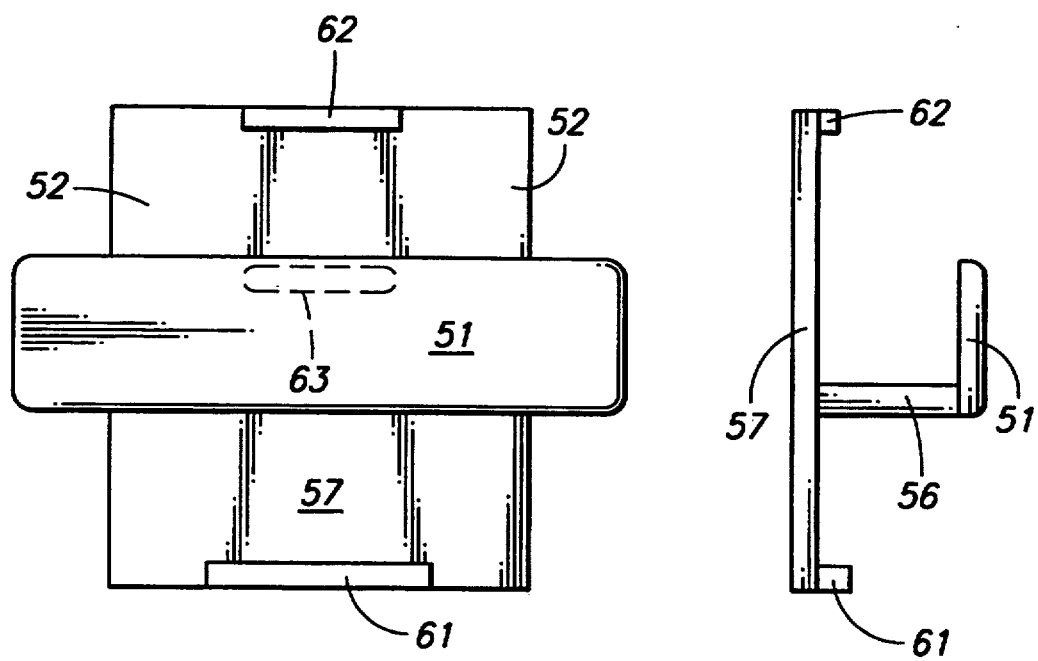
_Fig 16_     _Fig 17_

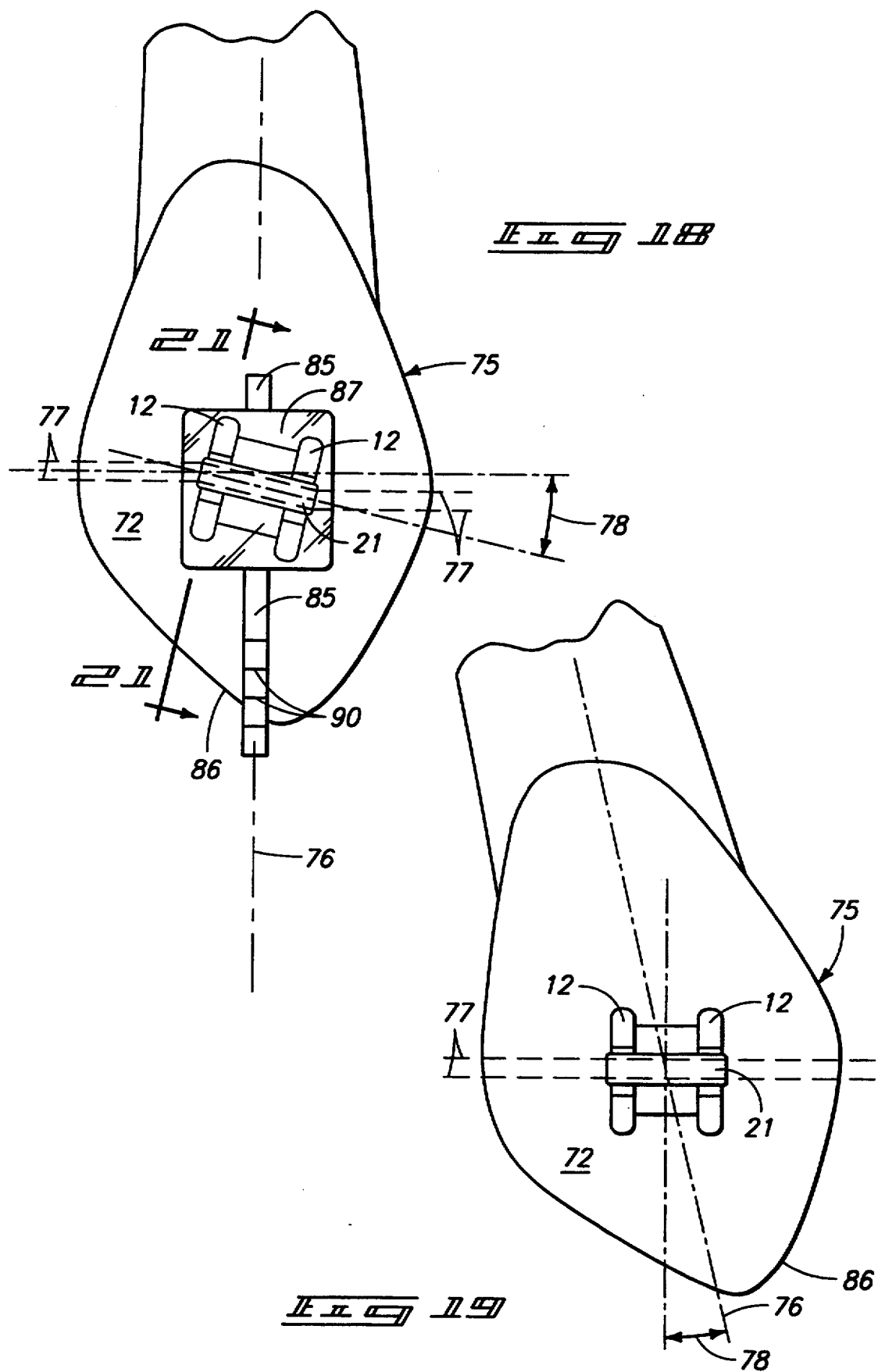

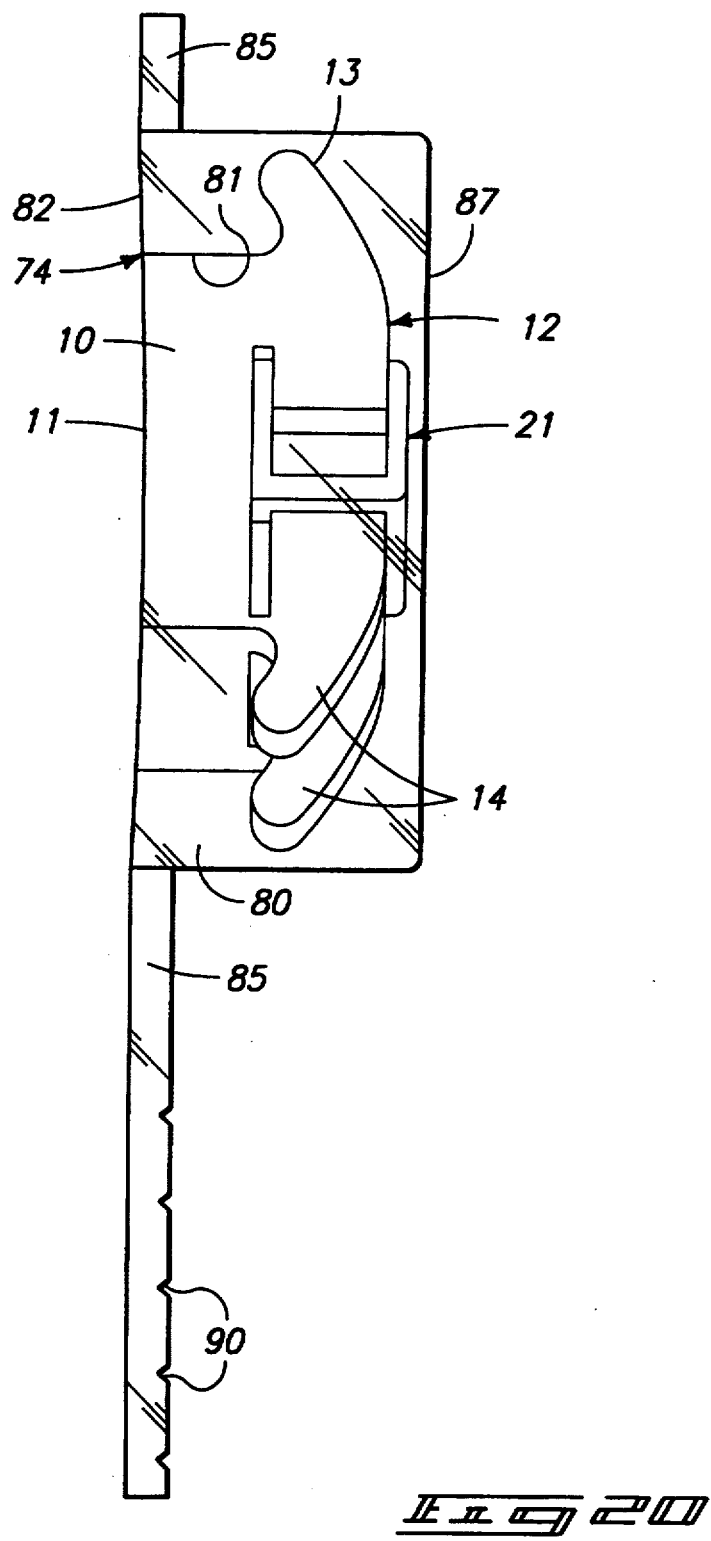

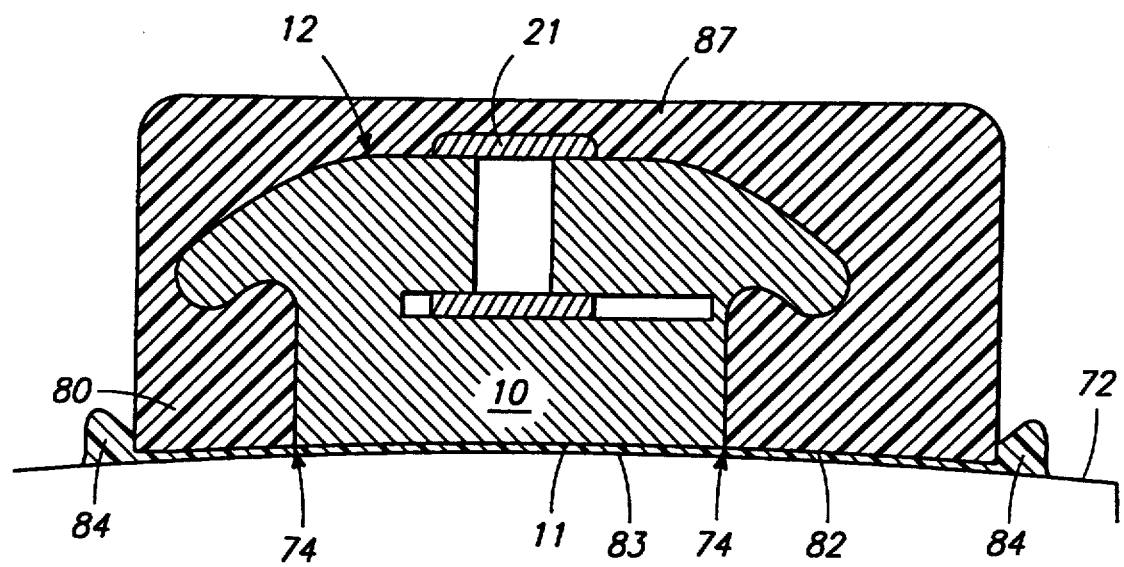
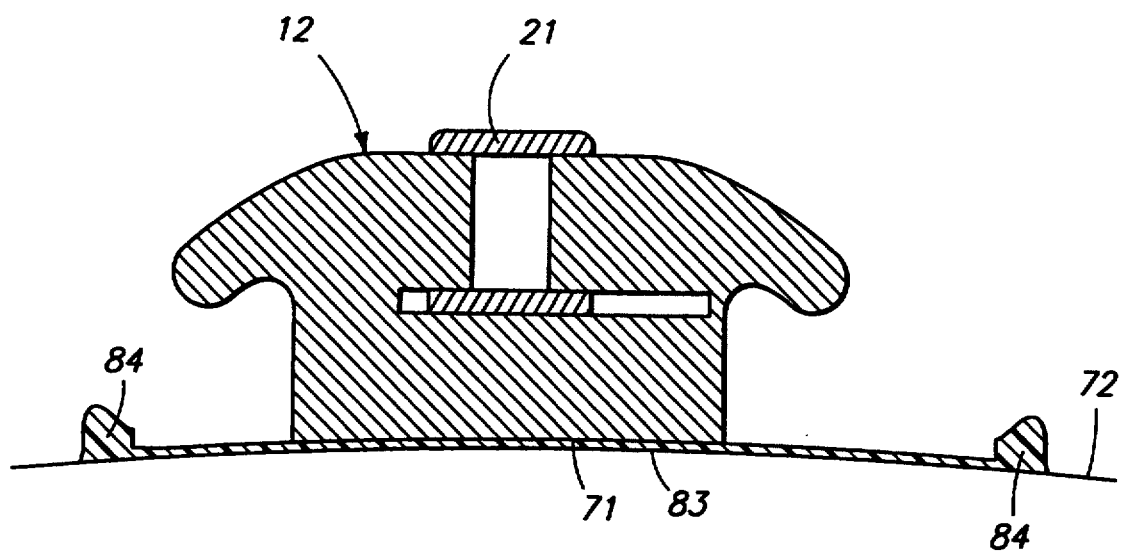

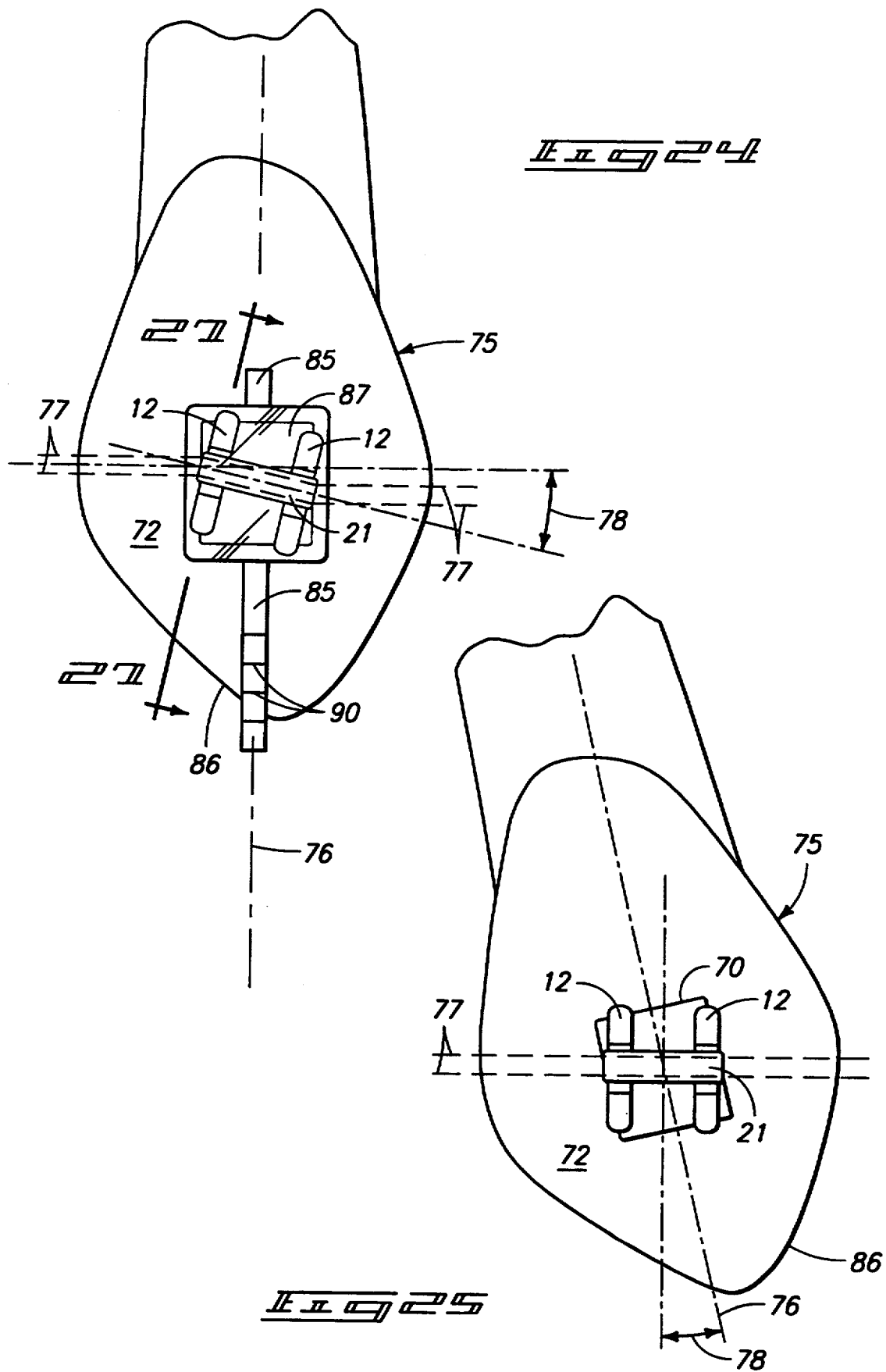

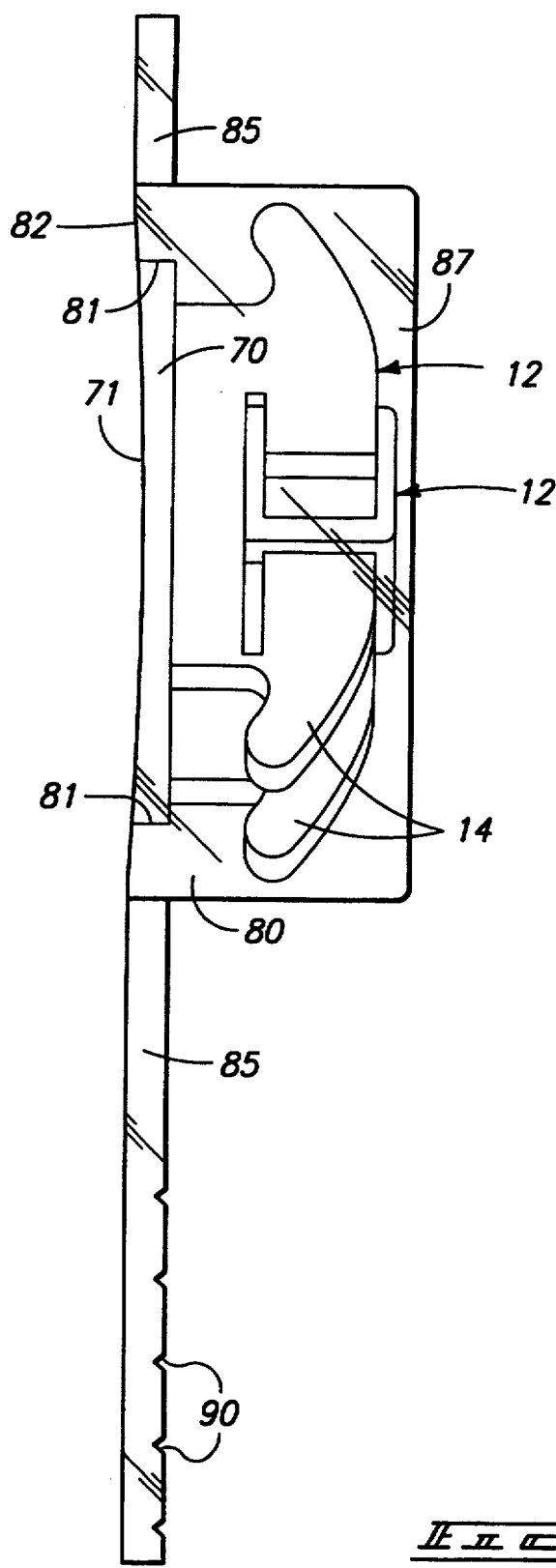

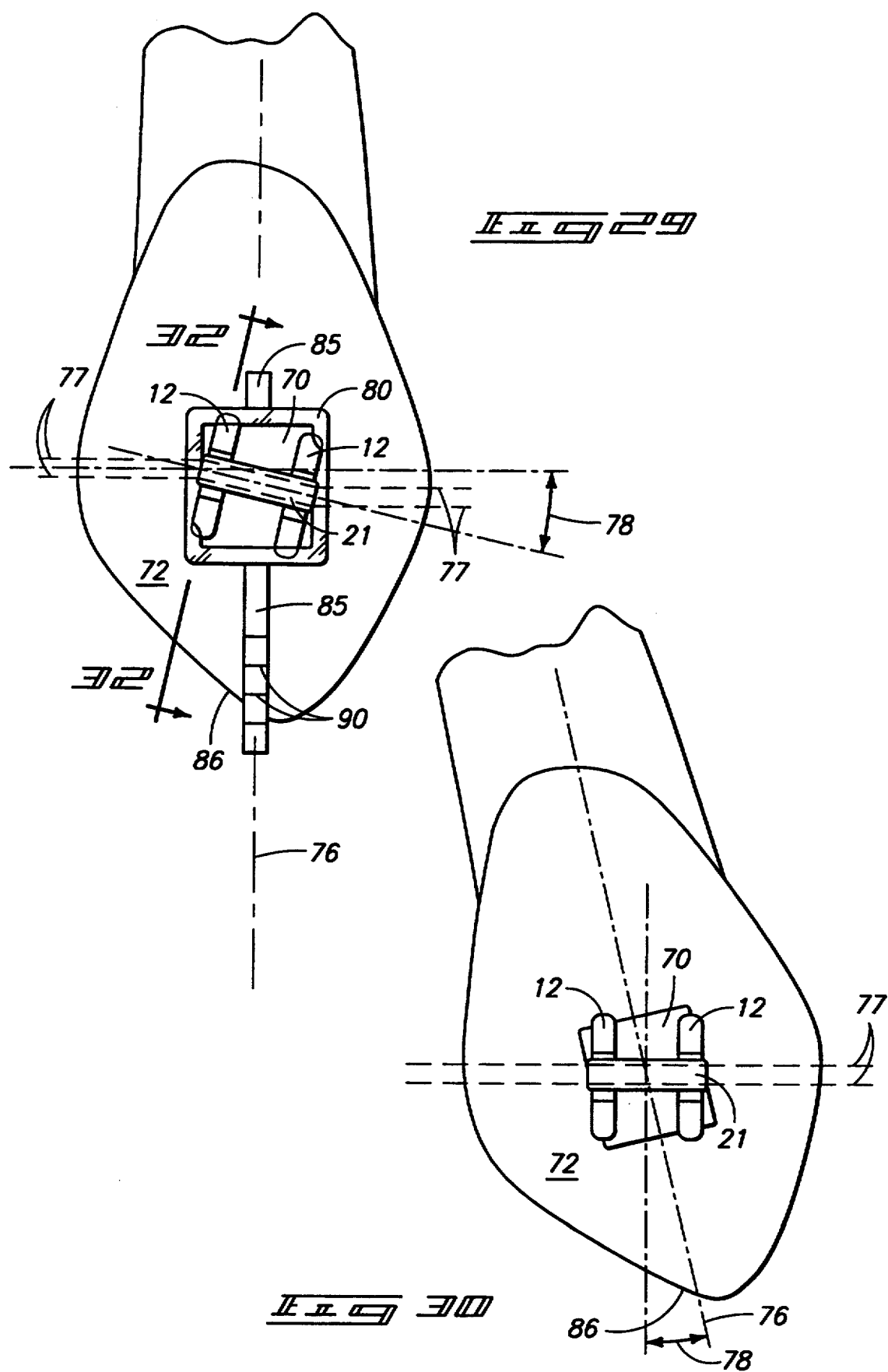

SELF-LOCKING ORTHODONTIC BRACKET

RELATED APPLICATION

This is a continuation-in-part of copending patent application Ser. No. 045,529, filed on Apr. 28, 1993, which is titled "Self-Locking Orthodontic Bracket" and is now U.S. Pat. No. 5,275,557, issued in Jan. 4, 1994.

TECHNICAL FIELD

This disclosure pertains to self-locking or ligatureless orthodontic brackets.

BACKGROUND OF THE INVENTION

Orthodontic brackets attached to teeth are adapted to engage an archwire that exerts forces upon them to move the teeth. Such brackets typically include an archwire slot for reception of the archwire. An archwire slot can have any desired cross-sectional configuration or size to match requirements of the archwire, or archwires, that are to be engaged within the slot.

Orthodontic brackets are typically bonded to a tooth or to a tooth band with the archwire slot oriented parallel to the occlusal plane. However, the slot can also be angularly oriented across the bracket when desired.

Most brackets in use today include extensions that project upwardly and downwardly at the top and bottom of the installed bracket, respectively. These extensions permit the archwire to be held within the archwire slot of the bracket by means of a twisted wire (ligature) or an elastomer O-ring.

Numerous attempts have been made to design brackets that are self-locking or ligatureless. A detailed discussion of patents and publications describing various closures that have been proposed for the archwire slots of such orthodontic brackets can be found in U.S. Pat. No. 5,094,614 to Wildman, issued Mar. 10, 1992, which is hereby incorporated into this disclosure by reference.

As recognized in the Wildman patent, an ideal locking device for an orthodontic bracket should leave the top and bottom of the bracket, including the projections conventionally Used for anchoring the tying wires, free to receive other attachments or auxiliary devices.

The Wildman patent discloses a slidable closure that engages the front of the archwire. The closure is recessed from the front or anterior surfaces of the disclosed bracket. This is also true of sliding closures shown in U.S. Pat. No. 2,671,964 to Russell et al., which was issued on Mar. 16, 1954 and in U.S. Pat. No. 3,131,474, which was issued on May 5, 1964 to Johnson. The fact that such recessed sliding closures require the archwire also to be recessed within the archwire slot before the closure can be moved over the archwire makes it very difficult for the user to visually confirm that the archwire is properly seated within the archwire slot to facilitate closing of the slidable cover.

When using a conventional bracket and tying wires, proper seating of the archwire can be confirmed by visually noting that the anterior surface of the archwire is flush with the anterior surface of the bracket. It is desirable that a self-locking bracket provide similar visual reference capabilities to the user. This cannot be attained where a sliding closure is recessed within the bracket.

A flush-mounted closure in the form of a spring clip is shown in various embodiments illustrated within U.S. Pat. No. 4,023,274 to Wallshein, issued on May 17, 1977. In FIGS. 4A and 4B of the Wallshein patent, there is illustrated a spring clip having a closure panel that extends across the full width of a bracket and covers aligned slots in two separate lugs. However, the spring clip also covers the bottom of the bracket and presents a separable bracket element that must be attached to the bracket prior to its utilization. A sliding closure is more easily manipulated than a spring clip. Slidable closures are particularly desirable because they substantially reduce the time required for opening and closing of the archwire slots during periodic adjustment of the archwire and brackets.

The present bracket was designed to mount an archwire flush with the anterior surface of an orthodontic bracket to facilitate visual positioning of the archwire during orthodontic treatment. It also was designed to utilize a sliding closure that is permanently retained on the bracket during use, whether the closure is left in an open or closed condition. This guards against accidental release of the closure while the bracket is worn on a tooth.

Most importantly, the closure has been designed to leave the usual tying extensions that protrude from the top and bottom of the bracket fully accessible to other orthodontic attachments to apply torsional forces to the teeth. The exposed tying lugs remain always available for repositioning of the bracket and tooth by use of tying wires or other conventional attachment systems.

The present bracket also includes a closure that completes a continuous tube surrounding the archwire when the closure is in a closed position. This can be effectively achieved in a Siamese bracket configuration without covering or interfering with projecting extensions on the bracket.

Creation of a continuous tube surrounding the archwire across the full width of the bracket eliminates the binding of the archwire within the confines of the bracket which occurs across the corners typically presented by conventional slotted bracket lugs.

In addition, the present closure lends itself to applications where the projecting lug structure of the bracket is angularly situated on a supporting base. By using a common lug structure on brackets having a plurality of archwire slot angles, a common closure can be used regardless of the slot angle. This substantially reduces the cost of producing the multiple brackets needed for orthodontic treatment purposes.

BRIEF DESCRIPTION OF THE DRAWINGS

Preferred embodiments of the invention are described below with reference to the accompanying drawings, which are briefly described below.

FIG. 1 is an elevational view of an assembled bracket with the cover in a closed position;

FIG. 2 is a side view of the bracket;

FIG. 3 is a side view of the bracket with the cover in an open position;

FIG. 12 is a bottom view of the bracket;

FIG. 13 is a sectional view taken among line 13—13 in FIG. 9;

FIG. 14 is a cross-sectional view similar to FIG. 13, showing the closure in an open position;

FIG. 15 is a side view of the bracket, illustrating use of a tying wire to retain the bracket on an archwire;

FIG. 16 is an elevational view of the closure;

FIG. 17 is a side view of the closure;

FIG. 18 is a front view illustrating installation of a bracket assembly including the first embodiment of the bracket;

FIG. 19 is a front view of the bracket in FIG. 18 following tooth adjustment;

FIG. 20 is an enlarged side view of the packaged bracket shown in FIG. 18;

FIG. 21 is an enlarged sectional view taken along line 21—21 in FIG. 18;

FIG. 22 is a view like FIG. 21 after removal of the encircling shield;

FIG. 24 is a front view illustrating installation of a bracket assembly including a third embodiment of the bracket;

FIG. 25 is a front view of the bracket in FIG. 24 following tooth adjustment;

FIG. 26 is an enlarged side view of the packaged bracket shown in FIG. 24;

FIG. 29 is a front view illustrating installation of a second bracket assembly including the second embodiment of the bracket;

FIG. 30 is a front view of the bracket in FIG. 29 following tooth adjustment;

DETAILED DESCRIPTION OF THE PREFERRED EMBODIMENTS

Figure 4:
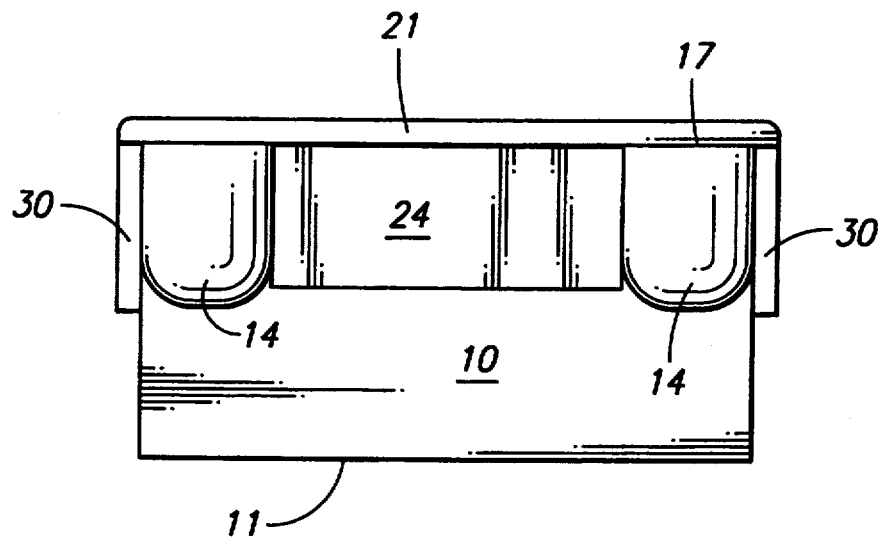
FIG. 4 is a bottom view of the bracket.

This disclosure of the invention is submitted in furtherance of the constitutional purposes of the U.S. Patent Laws "to promote the progress of science and useful arts" (Article 1, Section 8).

Three illustrative forms of the self-backing orthodontic bracket are illustrated in the drawings. A first preferred embodiment is shown in FIGS. 1–8 and 18–22. An alternative embodiment is shown in FIGS. 9–17. A third embodiment is shown in FIGS. 23–33.

When referring to the illustrated forms of the bracket, the front surfaces of each bracket, directed outwardly from a supporting tooth, shall be referred to as anterior surfaces. Conversely, the rear surfaces, which face toward the tooth, shall be termed posterior surfaces. Directions along the bracket generally parallel to the incisal or occlusal line shall be referred to as having width and being transverse. Conversely, perpendicular directions extending between the gingival line and the incisal or occlusal line shall be referred to as the height of the bracket. The upright surfaces across the bracket shall be termed its side surfaces and the surfaces along the top and bottom of the bracket shall be termed the incisal or occlusal surface or the gingival surfaces.

The incisal and occlusal surfaces, Or the gingival surfaces, of the bracket are normally interrupted by projections that form cleats or anchors for tying wires and other attachment devices. However, the basic features of the present improvement can be applied to bracket structures having no such extensions. The configurations of these extensions, when present, can take any desired conventional or unconventional form. The extensions at the top and bottom of the bracket can be located in different planes. The extensions at the top of the bracket can be located in a plane different from that of the extensions at the bottom of the bracket. The extensions might also have the same or a different configuration at the top of the bracket than at the bottom of the bracket.

Similarly, the archwire slot across each bracket can be oriented at any desired angular configuration relative to its incisal or occlusal surfaces to effect a desired degree of tipping to a supporting tooth. The archwire slots shown in FIGS. 1–17 of the illustrative drawings are aligned transversely across each bracket in a direction parallel to the incisal or occlusal surface for general illustration purposes.

In order to properly fit upon the exterior surface of a selected tooth, the posterior base surface across each bracket must be molded or otherwise formed to conform to the tooth with the archwire slot at the desired angular relationship to the archwire upon installation. Various placement angles can be provided on selected brackets by rotating the anterior surface contour across the bases of the brackets within a set. Alternatively, the archwire slots in a set of brackets can be arranged at selected angles by rotating the position of the protruding elements of each bracket relative to a common base structure having a properly contoured posterior base surface. The archwire slot is then formed on the protruding portion of the bracket to match the amount of tipping to be imparted to a given tooth. Such brackets are shown in FIGS. 23–33.

While the illustrated archwire slot is shown oriented perpendicular to the anterior surfaces of the bracket, it can be formed at any desired angle to the anterior surfaces, depending upon the desired torquing to which the supporting tooth is to be subjected.

The illustrated brackets can be bonded directly to a tooth or can be mounted on a tooth band for attachment to a tooth at either the facial or lingual tooth surfaces.

The present bracket can be made from any suitable material, including metals, plastics and ceramics, as well as a combination of such materials. The bracket and closure have generally been designed to be fabricated of metal, but the choice of materials is not critical to understanding or using this invention. The only limitation with regard to materials is the ability to efficiently fabricate or mold the bracket and closure as a cooperative mechanism to engage an archwire during orthodontic procedures.

The general concepts of the invention can best be understood from a study of the first embodiment of the assembled orthodontic bracket, illustrated in FIGS. 1–7. This form of the bracket includes a movable closure separately shown in FIG. 8.

The illustrated bracket includes a supportive base 10 having a posterior surface 11 adapted to be bonded to a tooth or tooth band. It is shown as a "Siamese" bracket, having two transversely spaced lugs or projections across the base 10. A single lug bracket, with or without protruding extensions, can alternately be used.

A pair of lugs 12 project anteriorly from base 10. While not limited to such applications, the lugs are shown as tying lugs. Each lug 12 includes opposed extensions 13 and 14 that project outwardly between transversely spaced side surfaces formed on the bracket. At a minimum, the tying lugs 12 each include an outer side surface 15. In addition, the tying lug configurations shown in the drawings further include inwardly facing side surfaces 16 formed across each tying lug 12.

The bracket also includes an anterior surface 17 across the front of each tying lug 12. The anterior surface 17 is illustrated as being planar, but can be curved if desired. It is interrupted by the opening of a transverse archwire slot formed distally from the anterior surface 17. The archwire slot spans the full width of the bracket, where it opens across the bracket side surfaces 15 (see FIGS. 2, 3 and 7).

The archwire slot includes side slot surfaces 18 and an anterior slot surface 20. The slot surfaces 18 and 20 are sized and configured in a manner complementary to the size and shape requirements of an archwire (or archwires) adapted to be received within the archwire slot. While the illustrated slot is rectangular and is designed specifically for reception of a complementary rectangular archwire, it is to be understood that the slot can be configured as a cylinder or other cross-sectional shape in the manner presently known with respect to orthodontic bracket design. In use, the dot is partially or completely filled by the cross-sectional configuration of one or more archwires located within it.

A closure complementary to the archwire slot is also provided on the illustrated bracket. It includes a movable cover 21 that slidably engages the anterior surface 17. Cover 21 has a width that spans the full width of the tying lugs 12 between the irrespective side surfaces 15. Its perpendicular width is greater than the corresponding width across the archwire slot at the anterior surface 17 of the bracket.

Figures 5, 6:
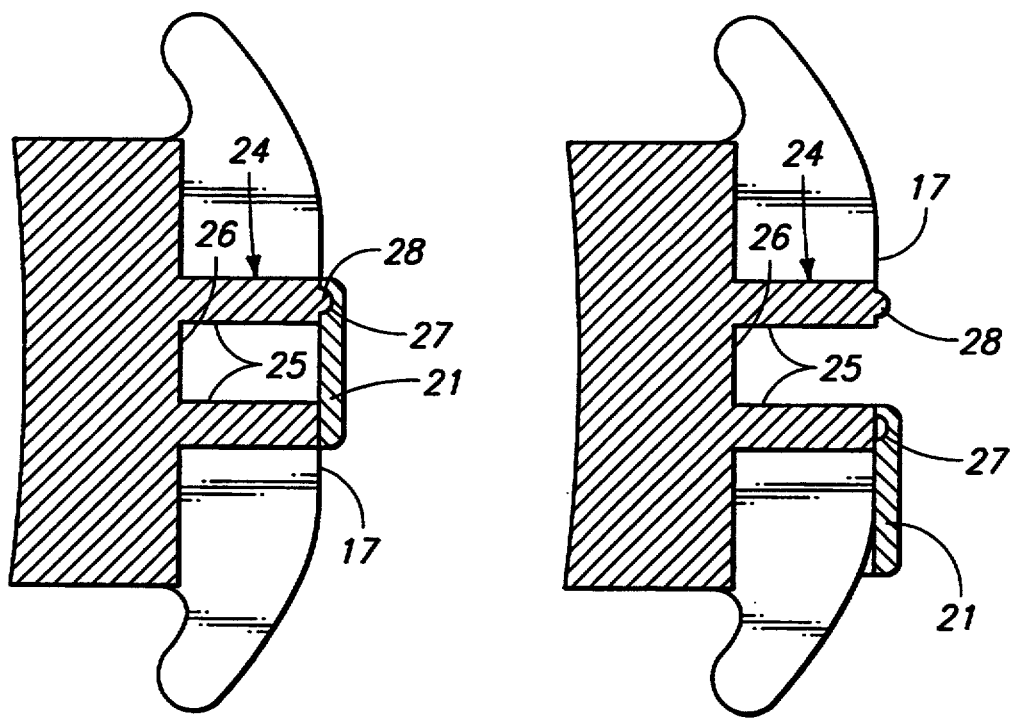
FIG. 5 is a sectional view as seen along line 5—5 in FIG. 1.
FIG. 6 is a sectional view similar to FIG. 5, showing the cover in an open position.

The closure further includes a pair of guides 22 spaced transversely apart from one another along the width of the bracket. The guides slidably engage opposed side surfaces 15 within complementary grooves 23. Movement of the cover and guides relative to the tying lugs 12 alternately positions the closure in (1) a first position with the cover clear of the archwire slot (FIGS. 2, 5) or (2) a second position with the cover 21 overlapping the width and height of the archwire slot (FIGS. 3, 6).

The above description includes only those elements basic to Siamese brackets, which include transversely spaced tying lugs protruding from a supporting base. However, additional strength and the benefits of an enclosed archwire tube can be imparted to this bracket by also providing a fixed transverse wall extending between the inner side surfaces 16 of the respective tying lugs 12. This wall, shown at 24, structurally interconnects the tying lugs 12 and base 10.

Wall 24 includes inner surfaces 25 aligned with the side slot surfaces 18 in the respective tying lugs 12. Either the wall 24 or base 10 also presents a perpendicular transverse surface 26 aligned with the anterior slot surfaces 20 along the respective tying lugs 12. The resulting open slot along the bracket is formed continuously from one side of it to the other, thereby eliminating the sharp edged corners that would otherwise be presented at the inner side surfaces 16 of the tying lugs 12.

Wall 24 is illustrated as a rather narrow structure spanning the two sides of the transverse archwire slot. However, it is to be understood that the thickness of wall 24 can be expanded to encompass the full height of the bracket across the illustrated base 10, while still leaving extensions 13 and 14 protruding openly at the top and bottom of the bracket.

Figure 7:
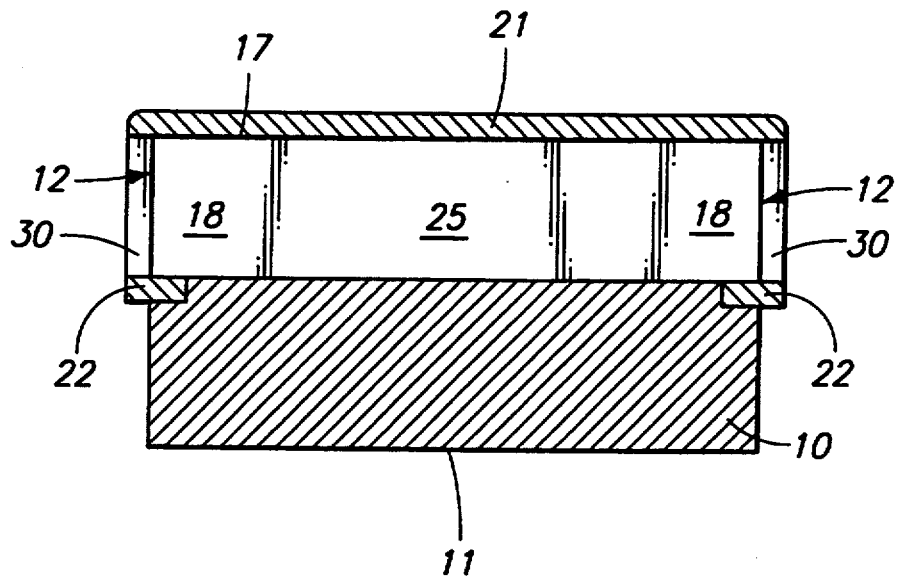
FIG. 7 is a sectional view taken along line 7—7 in FIG. 2.
Figure 8:
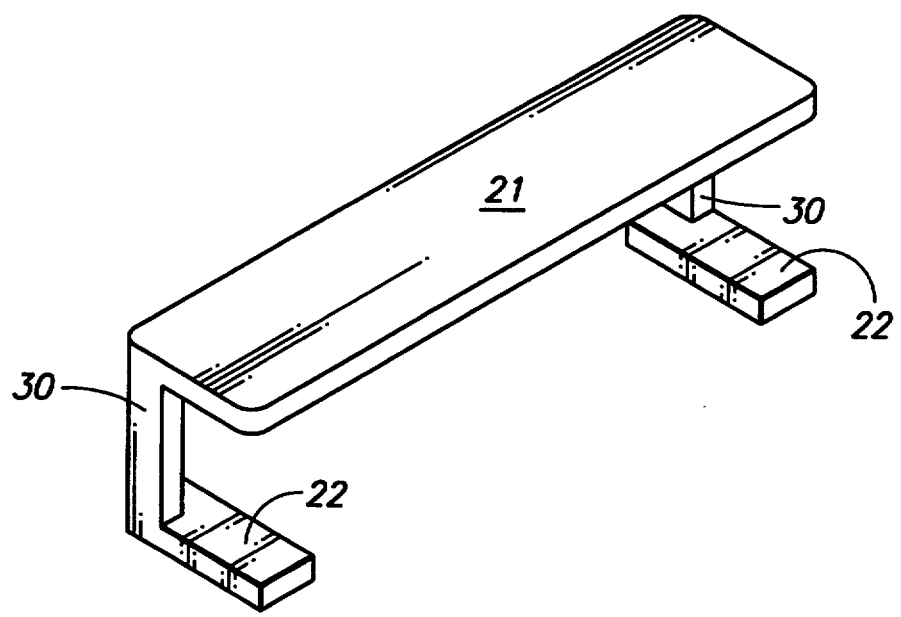
FIG. 8 is a perspective view of the closure shown in FIGS. 1-7.
Figure 9:
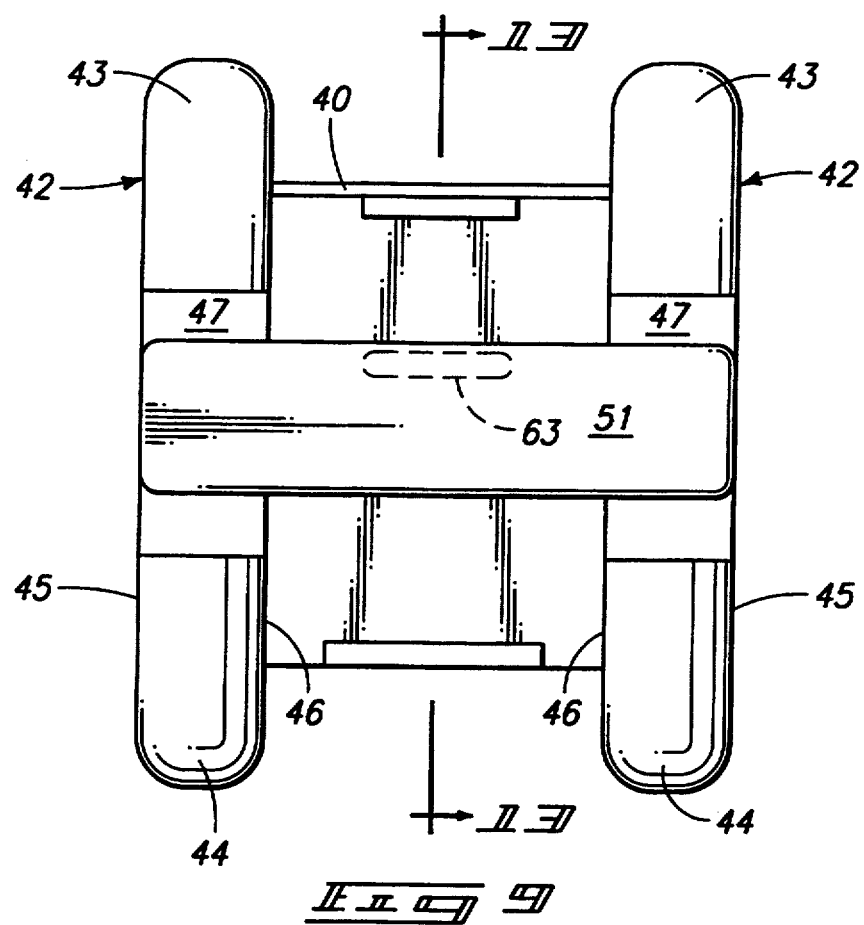
FIG. 9 is an elevational view of a second embodiment of the bracket.
Figures 10, 11:
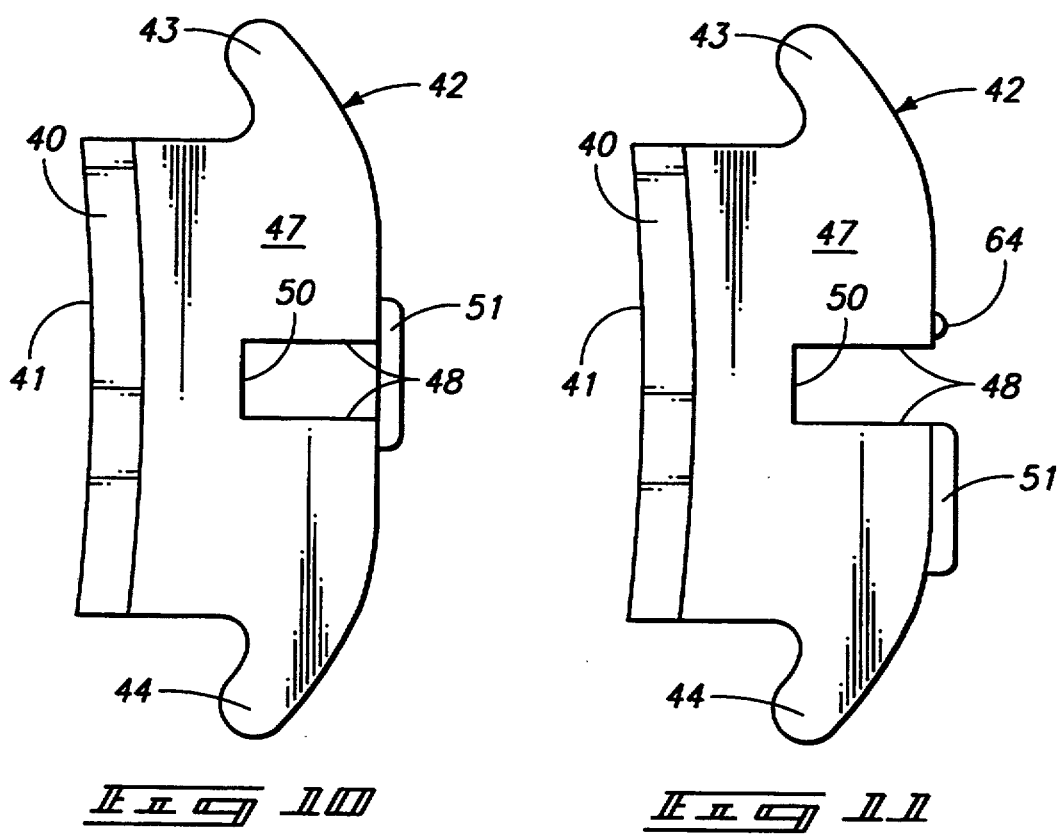
FIG. 10 is a side view of the bracket shown in FIG. 9.
FIG. 11 is a side view showing the closure in an open position.

As can be seen in FIG. 7, the side slot surfaces 18 along the tying lugs 12 and the inwardly facing surfaces 25 within transverse wall 24 merge to form continuous inner slot surfaces extending across the full width of the bracket. They intersect similarly merging anterior slot surfaces 20 and 26, as previously described. When enclosed by cover 21, as shown in FIGS. 2 and 5, these surfaces and the movable cover form a fully enclosed tube for engagement of an archwire across the complete width of the bracket.

Cover 21 and guides 22 are structurally interconnected by an interposed pair of rigid support members shown at 30. The support members 30, together with cover 21 and guides 22 form a separable closure generally illustrated in FIG. 8. This closure can be molded or fabricated independently from the bracket. It should be assembled on the bracket prior to installation of the bracket on a tooth or tooth band. While the closure is normally retained on the bracket during its use, it can be forced free from the bracket for replacement purposes or when use of the closure is not required. The design of the bracket and closure should be such that removal of the closure can only be achieved by substantial prying movement, such as might be applied through use of a scaler.

It is preferable that cover 21 be releasably locked in its closed position to ensure against accidental release of an archwire received within the archwire slot. Releasable detents or locks can be provided between the cover 21 and the bracket or between the guides 22 and the bracket. As an illustrative locking device, the open edge of cover 21 has an inwardly recessed groove 27 formed along its transverse center. The groove 27 releasably engages a complementary ridge 28 formed along the transverse center of the overlapped anterior surface of transverse wall 24. While generally rigid, the cover 21 must then have sufficient flexibility to yield slightly to ride over the ridge 28 as the cover 21 is moved between its operative positions.

It is also desirable that cover 21 not be accidentally released from engagement with the supporting bracket structure while within the mouth of a patient. This can be achieved by provision of positive stops on the guides 22 to limit their extent of sliding movement along the receiving grooves 23. Removal of cover 21 might also be prevented by protrusions (not shown) that extend outwardly from side surfaces 15 in the path of the rigid support members 30 that interconnect cover 21 and guides 22. In the embodiment illustrated, outward movement of cover 21 is limited by the extent of groove 27, which terminates short of the adjacent side edge along the bracket. The design and operation of these detents, locks and motion limiting features is subject to many variations and are not essential to an understanding of the present invention.

The bracket and closure are preferably mounted on a tooth with the open edge of the closure facing toward the gingival line. Thus, biting pressures on food will tend to maintain the closure in a closed condition over the archwire received in the archwire slot.

The support members 30 are respectively located adjacent to the side surfaces 15 across the tying lugs 12. Each support member 30 leads posteriorly from the cover 21 to one of the guides 22.

The sliding guides 22 are illustrated as being parallel to the portions of the anterior surface 17 slidably engaged by cover 21. Thus, the movement imparted to the supported cover 21 will maintain it in a parallel position with its inner surface flush against the overlapped areas of anterior surface 17. This will maintain cover 21 in a closely adjacent position to the stationary bracket structure regardless of whether cover 21 is in its open or closed positions. If the anterior surface 17 is transversely curved, the guides 22 and grooves 23 might be similarly curved to achieve the desired flush sliding relationship between surface 17 and cover 21.

When in its open position, as shown in FIGS. 3 and 6, cover 21 will leave the slot clear for movement of an archwire into or out from the slot. In addition, the protruding extensions 13 at all times remain clear and accessible for tying or attachment purposes.

Guides 22 are located on the bracket in positions that are posterior to the open slot formed transversely through it, As can be seen in FIGS. 2 and 3, the support members 30 are offset from the center line of the closure to assure that there is adequate clearance across the full width of the archwire slot when the cover 21 is in its closed position. Thus, transverse sliding movement of the guides 22 and support members 30 does not block or restrict access to any portion of the open transverse archwire slot.

FIGS. 9-17 illustrate a second form of the invention in which the transverse separation of the tying lugs across the supportive base is more pronounced. The elements of the bracket and cover common to those previously disclosed herein will not be described again in repetitious detail.

The second embodiment of the improved bracket also includes a mounting base 40 having a posterior surface 41. A pair of transversely spaced tying lugs 42 project anteriorly from base 40. They include extensions 43 and 44, which project from the bracket between outer and inner side surfaces 45 and 46 across the tying lugs 42.

An anterior surface 47 is presented along the front of the bracket across the respective tying lugs 42. An archwire slot extends transversely through each tying lug 42. It includes side slot surfaces 48 and a anterior slot surface 50.

The closure as shown in FIGS. 9-17 includes a movable cover 51 supported by a pair of guides 52. The guides 52 are slidably engaged within complementary grooves 53 formed across the inner side surfaces 46 of the respective tying lugs 42. Grooves 53 and guides 52 are located posteriorly with respect to the anterior slot surface 50 of the archwire slot.

A transverse wall 54 spans the two tying lugs 42. It is preferably molded integrally with the tying lugs 42 and base 40. An inner surface 55 along wall 54 is aligned with lone side slot surface 48 as an integral extension of it, thereby forming a continuous side slot surface extending the full width of the illustrated bracket.

The closure of the second embodiment, like that of the first, has a structure that is complementary to the archwire slot. Since the inner surface 55 of transverse wall 54 is coextensive and flush with at least a portion of the inner archwire slot surfaces, namely one side slot surface 48, the remaining surfaces required to complete the archwire slot in the space between tying lugs 42 must be supplied by the movable closure. As shown, these surfaces are provided on support members 56 and 57 that structurally interconnect cover 51 to guides 52.

In the illustrated embodiment, structural member 56 is perpendicular to the attached cover 51. It has an inner surface 58 aligned with the remaining side slot surface 48 along the archwire slot. Structural member 57 is a shelf arranged in a position that is parallel to cover 51. Guides 52 are formed as outward extensions along its opposed sides. An inner surface 60 along structural member 57 is aligned with the anterior slot surface 50 of the archwire slot when the cover 51 is in its closed position.

Structural member 57 is also provided with an upturned side 61 that can serve as a manual handle or grip to facilitate opening or closing of cover 51 relative to the supporting orthodontic bracket. The opposite side of structural member 57 is shown with an upturned central section 62 that can serve as a stop capable of abutting transverse wall 54 and limiting the extent of opening movement that can be imparted to cover 51.

An inwardly facing central groove 63 adjacent to the free edge of cover 51 and a complementary ridge 64 across the top central section of transverse wall 54 are illustrative of a detent or lock for maintaining cover 51 in its closed position overlapping the archwire slot.

The above two embodiments are intended to merely illustrate the basic structural features of the improved orthodontic bracket. In both, the closure that completes the archwire slot comprises a slidable mechanism supported on the bracket at a location that is behind or posterior to the archwire slot boundaries. Sliding support for the closure can be provided either along inwardly facing side surfaces or outwardly facing side surfaces of the bracket. In both arrangements, the closure is movable between a first position clear of the archwire slot and a second position overlapping the its width and height.

When used in conjunction with a bracket design that further includes at least a portion of the slot structure between spaced tying lugs, the closure can also supply complementary surfaces movable between the lugs to fully complete a continuous archwire tube across the full width of the bracket.

In both embodiments, the closure does not impede normal access to and use of the tying lugs. The extensions that protrude to the sides of the orthodontic bracket remain unobstructed at all times. The bracket can therefore be used to apply torsional forces to a tooth to rotate it about a desired axis or to use ligatures to interconnect the bracket and archwire where this is required. As an example, FIG. 15 illustrates the use of a tie wire 65 wrapped about extensions 43 of the second illustrated embodiment of the invention.

A conventional tie wire 65 might be used to secure the bracket to an archwire 66 when the current position of the attached tooth is such that the archwire 66 cannot be completely positioned within the archwire slot of the bracket at a particular stage during orthodontic treatment. By leaving the closure open and using tie wires 65 to move the tooth relative to the archwire 66, a practitioner can utilize the present bracket at treatment stages priori to that at which use of the self-locking feature of the bracket becomes practical. Similarly, tying wires, bands and other devices can be attached to the extensions of the bracket at any time to apply rotative forces or attach other orthodontic devices to the bracket.

In the preferable forms of the invention, where the closure completes a continuous tube that can surround an archwire along the full width of the bracket, the tube structure eliminates the corners conventionally encountered along the slotted lugs on dual or Siamese orthodontic brackets. These corners typically exert binding forces on the archwire, which impede tooth movement by the resulting concentration of frictional forces along the width of the archwire. The continuous tube formed by the preferred forms of this invention assures freedom of movement of the bracket relative to the archwire, thereby increasing the rate of tooth movement and reducing the need for frequent manual readjustment of the brackets during treatment.

An important result of the present invention is the fact that the archwire, when properly received within the archwire slot of the bracket, is at least flush with the outer or anterior surface of the bracket. Proper reception of the archwire within the receiving archwire slot and the ability to close the cover over the archwire can therefore be readily confirmed by visual inspection of the bracket within the mouth. This is contrasted with the difficulty of gauging the archwire positions within earlier brackets having slidable closures recessed beneath the anterior surface.

Packaged orthodontic bracket assemblies that facilitate alignment and installation of the bracket are illustrated in FIGS. 18–22 and 24–33. The brackets included in these novel bracket assemblies are not to be limited to the illustrated siamese brackets. They might include any form of orthodontic bracket, whether or not it includes lugs, tying extensions or archwire slots.

FIGS. 18–22 show a packaged bracket assembly including the first embodiment of the bracket as shown in FIGS. 1–8. Identical reference numerals are used in FIGS. 18–22 to identify the pertinent elements of the bracket structure previously described with respect to FIGS. 1–8. FIGS. 24–33 show two different packaged bracket assemblies including a modified third embodiment of the bracket illustrated in FIG. 23.

Referring to FIGS. 19–22, the basic packaging feature of the bracket assembly comprises a shield 80 that is removably mounted to the base 10 of the bracket. Shield 80 has one or more inner surfaces 81 complementary to corresponding surfaces about the periphery of base 10.

The periphery of base 10 is illustrated as being rectangular, but can be designed and constructed with any geometrical configuration suitable for attachment to a supporting tooth surface.

Shield 80 is preferably molded or formed from flexible resin or rubber material capable of conforming to and frictionally engaging the side surfaces of base 10 about the bracket. It can be solid and engage all exposed surfaces of the bracket, as shown, or it can be hollow and encompass the bracket.

The inner surfaces 81 of shield 80 are juxtaposed against their corresponding surfaces about the periphery of base 10. The resulting tight fit between the inner surfaces 81 of shield 80 and the corresponding planar sides of base 10 prevents adhesive from flowing between them as base 10 is manually pressed into place on a supporting tooth.

In the preferred embodiment, the inner surfaces 81 of the shield 80 terminate along an outer edge 82 flush with the intersection of the base periphery and the posterior base surface 11. This intersection is indicated in the drawings by arrows 74.

The primary purposes of shield 80 are to prevent adhesive from flowing along the base 10 and lugs 12 as the adhesive flows outwardly from beneath the posterior base surface 11 in response to mounting pressure applied to the bracket and to assist in manually placing and aligning the bracket on a supporting tooth.

By partially or completely surrounding base 10 with an engaging shield 80, any resulting flow of excess adhesive from beneath the base 10 can be diverted outwardly and away from the bracket, as illustrated in FIGS. 21 and 22. These figures show a layer of adhesive 83 between tooth surface 72 and the posterior base surface 11 of the bracket. Removal of excess adhesive from the bracket in the absence of a surrounding shield can be a difficult task. Any such adhesive on the exterior of the bracket might subsequently interfere with placement of an archwire within the bracket archwire slot and required movement of closure 21.

As the layer of adhesive 83 spreads outwardly in response to application pressure exerted on the bracket, it will flow beneath the outer edges 82 of shield 80. The excess adhesive will form beads 84 physically spaced from the bracket by a dimension equal to the thickness of shield 80 adjacent to its outer edge 82. The resulting space between these beads 84 and the periphery of base 70 after removal of the shield 80, which can he seen in FIG. 22, facilitates subsequent engagement of the beads of adhesive 84 by a scraper or other removal tool.

As shown in FIGS. 20–22, a protective cap 87 is formed integrally with the shield 80 to overlap both the base 10 and the lugs 12 of a selected orthodontic bracket. The complementary cap protects the bracket from external contamination as it is being handled. Shield 80 and cap 87 also enlarge the exterior of the bracket to facilitate its handling by a tool or by the fingers during placement on a tooth. The shield provides a consistent exterior configuration for brackets of various angular orientations. It also presents common peripheral surfaces that surround the base of a bracket to assist in visually relating the bracket to the long axis of a supporting tooth regardless of its archwire angles.

The cap 87 and shield 80 are preferably produced from transparent material, permitting the bracket to be viewable through the overlying cap 87 in the assembled bracket package. However, cap 87 can alternately be constructed of translucent or opaque material, particularly where color coding of the cap is used to facilitate bracket identification. Printed indicia can also be applied to the exterior of cap 87 for bracket identification.

The protective cap 87 and shield 80 provide a consistent bracket package to facilitate manual handling and placement of different selected brackets along a row of teeth. The intended orientation of the bracket on a tooth can be visually confirmed by inspection of the bracket through the covering cap 87 when the cap is made from transparent or translucent material.

Shield 80 and cap 87 can be readily removed after placement of the bracket on a tooth. This is accomplished by simply stretching and peeling the flexible shield and cap apart from the mounted bracket. The exposed bracket will then remain attached to the tooth, as illustrated in FIG. 19, which shows the mounted bracket after tooth movement as a result of the tipping forces exerted on tooth 75 by the bracket mounted as shown in FIG. 18.

The shield 80 also includes a pair of aligned extensions 85 that protrude outwardly within a plane substantially parallel to the posterior base surface 11 of the bracket. One elongated extension 85 further includes visible indicia 90 which are intended to indicate the location of base 10 and the bracket relative to the anterior surfaces 86 of a supporting tooth 75 (see FIGS. 18, 19). The illustrated extensions 85 are aligned parallel to the intended alignment of base 10 relative to the long tooth axis 76 of a supporting tooth 75. Correspondence between the extensions 75 and the long tooth axis will result in angular placement of the archwire slot across the bracket at an angle 78 corresponding to the tipping angle at which the bracket is to be initially engaged by an archwire, shown by lines 77 in FIGS. 18 and 19.

Extensions 85 facilitate alignment and proper placement of the orthodontic bracket on a tooth for alignment along an engaged archwire. While the orthodontic brackets could be aligned visually, the provision of the shield 80 and cap 87 plus extensions 85 greatly simplifies the installation process and improves placement accuracy in a mounted group of brackets that are to be engaged by a common archwire.

Figure 23:
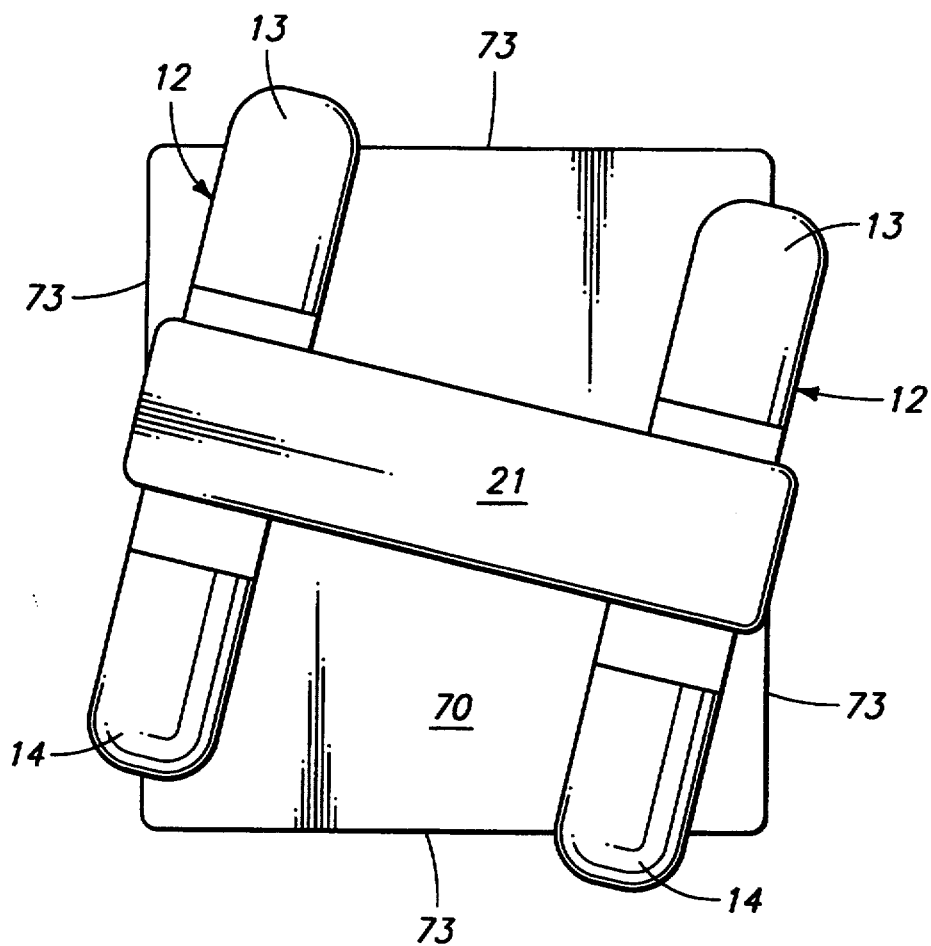
FIG. 23 is an elevational view of a second embodiment of the bracket.

FIG. 23 illustrates a further modification of the previously-described bracket. The orientation of the archwire slot shown in this embodiment is angularly positioned on a common base 70 to apply tipping forces on a supporting tooth when the bracket is engaged in the mouth by a conventional archwire.

The protruding lug structure, archware slot, and closure illustrated in FIG. 23 are substantially identical to the corresponding features of the bracket shown and described with respect to FIGS. 1–8. However, the base 70 of the bracket is constructed as a flange having an posterior base surface contoured to match the supporting tooth surface on which the bracket is to be adhered. Identical reference numbers have been used within FIGS. 23–33 to denote features common to the embodiments of the invention in FIGS. 1–8 and 18–22.

The bracket modification illustrated in FIG. 23 facilitates design and manufacture of matched bracket sets for applying various tipping forces to teeth as they are being adjusted in the mouth. This angular bracket design permits efficient manufacture of similar brackets having various archwire slot angles, but using a common lug and cover configuration. The use of a common lug structure reduces molding costs and permits one construction of the cover 21 (shown in FIG. 8) to be used on all embodiments of the illustrated brackets, regardless of the tipping angle provided by use of a particular bracket.

The orientation of lugs 2 at an angle relative to the supporting base 70, as shown in FIG. 23, eliminates any increase in lug width to accommodate the greater amount of sliding travel that cover 21 would otherwise require to overlap an oblique archwire slot formed across the sides 15, 16 of lugs 12 in FIGS. 1–8.

The base 70 of the modified bracket has a periphery that intersects a posterior base surface 71 (see FIGS. 27, 28) adapted to be bonded to a supporting tooth. Surface 71 is contoured to match the abutting tooth surface when the base 70 is properly aligned relative to the long tooth axis, which is schematically illustrated in FIGS. 24 and 25 by the line 76. The formation of such complementary mounting surfaces is well known in the design of orthodontic brackets, and will not be further described herein.

In this embodiment, the archwire slot and protruding lugs are rotated about the base and contoured posterior base surface 71 to present the archwire slot at the desired angular position relative to the long axis of a tooth.

Figure 27:
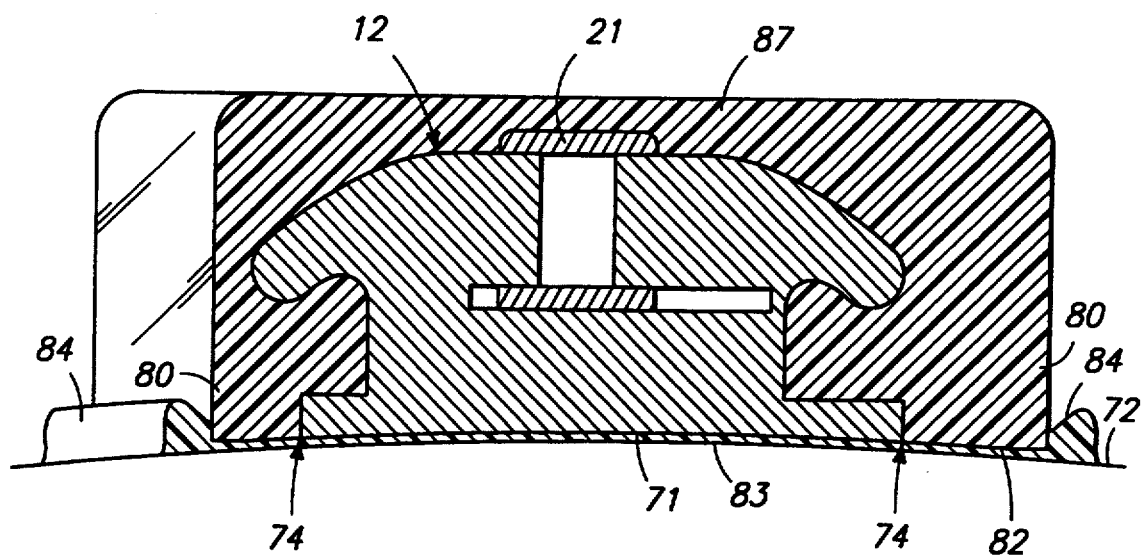
FIG. 27 is an enlarged sectional view taken along line 27—27 in FIG. 24.
Figure 28:
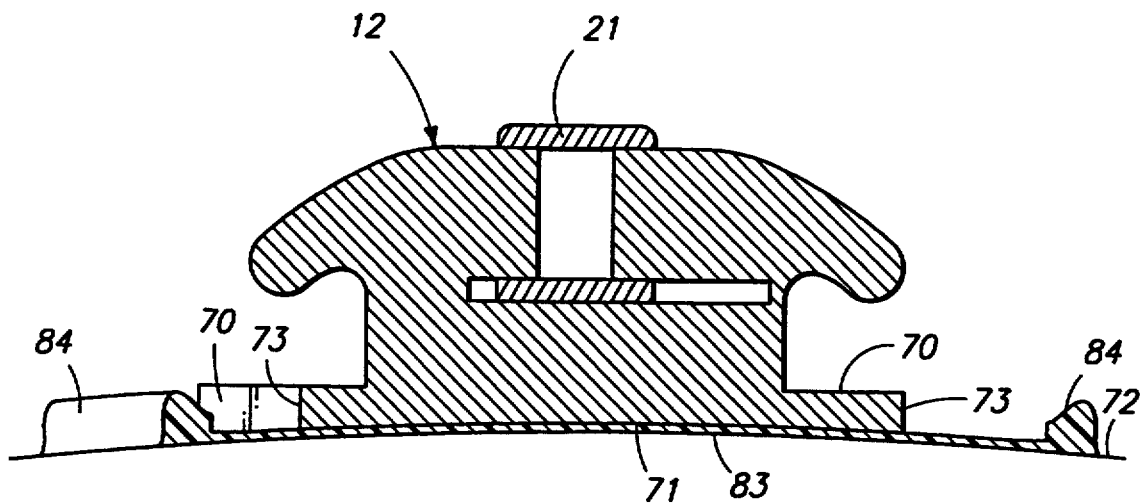
FIG. 28 is a view like FIG. 27 after removal of the encircling shield.
Figure 31:
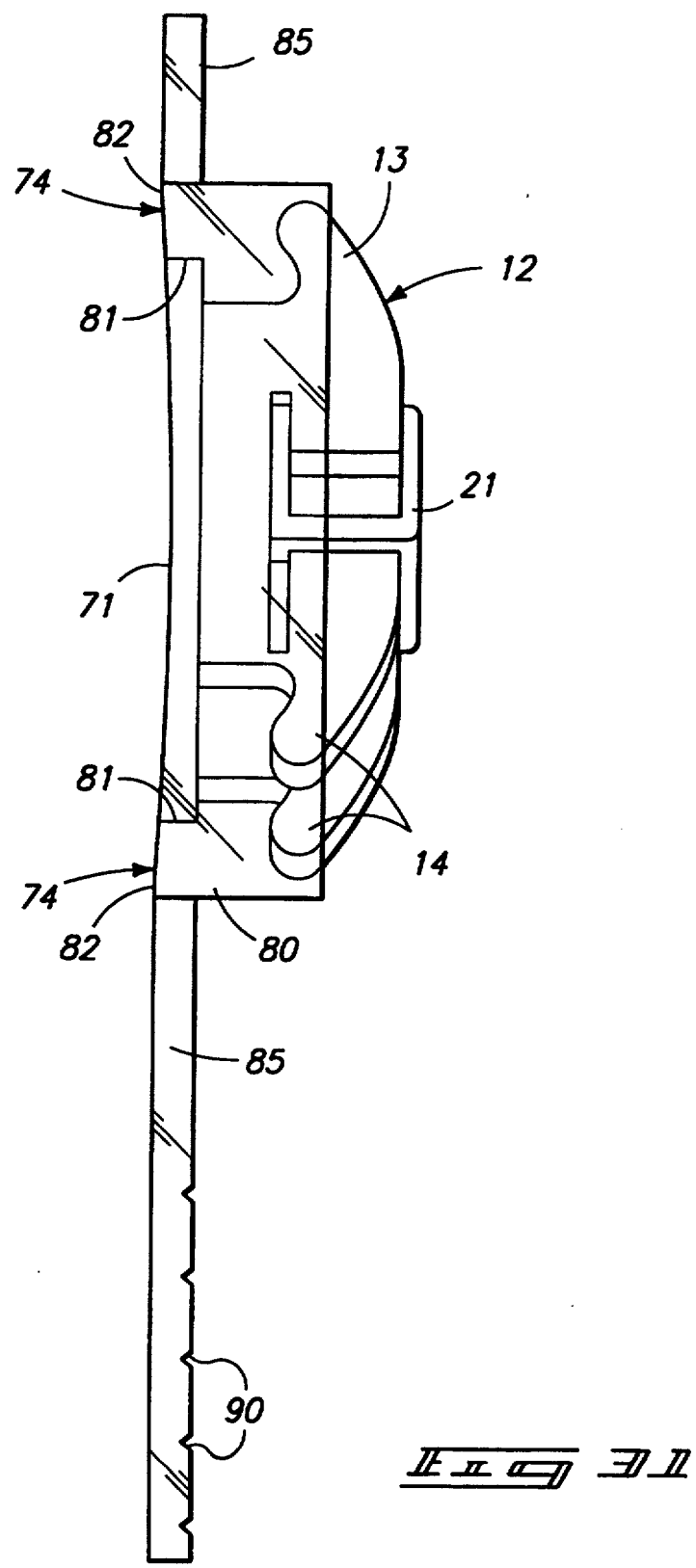
FIG. 31 is an enlarged side view of the packaged bracket shown in FIG. 29.
Figure 32:
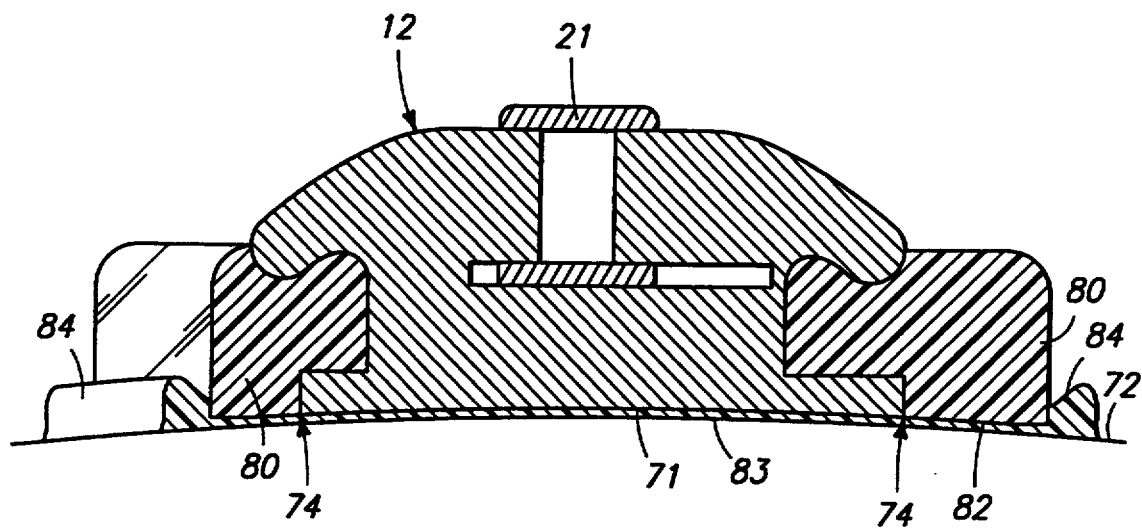
FIG. 32 is an enlarged sectional view taken along line 32—32 in FIG. 29.
Figure 33:
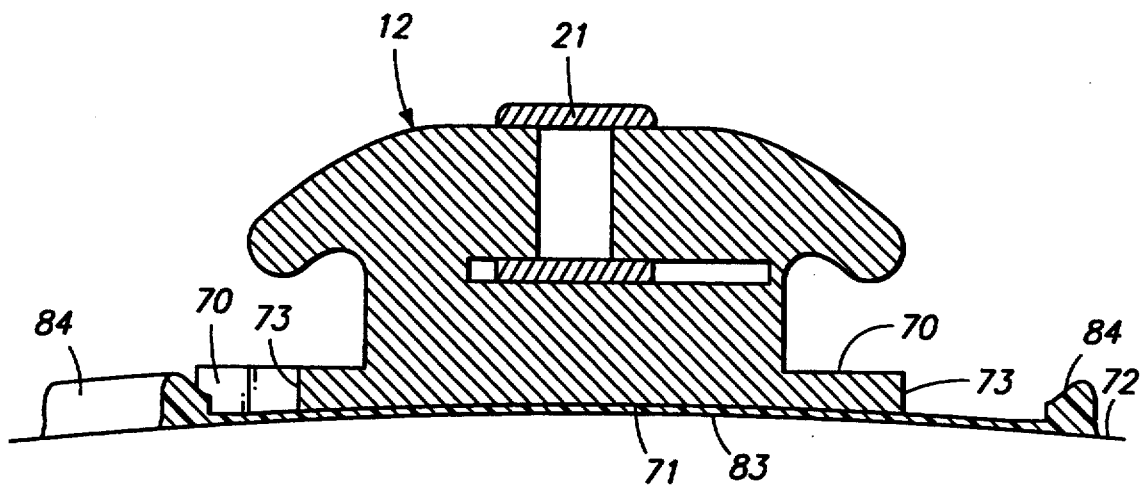
FIG. 33 is a view like FIG. 32 after removal of the encircling shield.

The periphery of the illustrated bracket base 70 is rectangular. It is formed with four planar sides 73. Each side 73 about the periphery of base 70 leads to an intersection between the periphery and the posterior base surface 71, which are illustrated in FIGS. 27, and 32 by arrows 74.

The orientation of the archwire slot across the anterior surfaces of lugs 12 is perpendicular to the lug side surfaces 15, 16. However, to exert a tipping force on a supporting tooth when the upright sides 73 of base 70 are aligned along the long tooth axis, the archwire slot is also arranged in a position that is oblique relative to the planar sides 73 of base 70.

FIGS. 24 and 25 illustrate tipping of a supporting tooth 75 by initial placement of base 70 with its upright planar sides 73 arranged parallel to the long tooth axis (denoted by line 76). The initial position of an engaged archwire is schematically illustrated by dashed lines 77. The desired tipping angle prior to tooth movement is shown in FIG. 24 and is indicated in the schematic drawings by the number 78.

FIG. 25 illustrates the tooth 75 after the archwire slot has been oriented parallel to the archwire 77, and visually shows the long tooth axis 76 having been tipped by the same angle 78.

While the periphery of base 70 illustrated in FIGS. 23–33 is shown as being rectangular (which includes a square configuration), it is to be understood that the base periphery might be circular or oval, and can be designed and constructed to have any desired geometrical configuration.

Aligning means is provided on the base 70 for indexing it in relation to the long tooth axis of a supporting tooth. This can be provided by one or more planar peripheral surfaces, as illustrated by the planar sides 73, or by visual indicia (not shown) to assist the user in properly orienting the bracket on a tooth during installation. Proper installation of the bracket to exert desired forces on a tooth, using conventional adhesive techniques, will be self-evident to those skilled in designing and using orthodontic brackets.

Referring now to the bracket assembly shown in FIGS. 24–28, the packaging features illustrated with respect to use of the third embodiment of the bracket correspond directly with those features shown in FIGS. 18–22, respectively. Both the protective shield 80 and cap 87 are shown in this set of drawings. FIGS. 29–33 similarly show an alternate package including an annular shield 80 without a covering cap. The purposes and operation of shield 80 are substantially identical to the purposes and operation as previously described where the shield is integral with a cap.

The inner surfaces 81 of shield 80 are rectangular in the illustrated embodiments of FIGS. 24–33. The annular shield 80 is sized to frictionally engage the planar sides 73 about the periphery of base 70. The inner surfaces 81 of shield 80 are juxtaposed against their corresponding surfaces about the periphery of base 70. The resulting tight fit between the inner surfaces 81 of shield 80 and the planar sides 73 of base 70 prevents adhesive from flowing between them as base 70 is manually pressed into place on a supporting tooth.

While extensions 85 are aligned parallel to the illustrated upright sides 73 of base 70, they can alternately be aligned perpendicular to the archwire slot of the bracket with which they are associated. In addition, one extension 85 can be eliminated where not desired in a particular bracket package. Various minor changes can obviously be made in such details without deviating substantially from the essentials of the described invention.

In compliance with the statute, the invention has been described in language more or less specific as to the illustrated features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A self-locking orthodontic bracket, comprising:
a base having a posterior surface adapted to be bonded to a tooth;
a pair of lugs projecting anteriorly from the base in transversely spaced parallel positions;
the lugs including anterior surfaces, interrupted by flush openings leading to an archwire slot formed digitally from the anterior surfaces, the slot including aligned inner slot surfaces across the lugs;
a fixed wall extending between the lugs, the fixed wall having a surface coextensive and flush with at least a portion of the slot surfaces;
a movable cover overlapping the anterior surfaces of the lugs, the cover having a width that spans the full width of the pair of lugs and a perpendicular height that is greater than the height of the openings of the archwire slots across the anterior surfaces; and
guide means slidably supporting the cover on the pair of lugs for alternately positioning the cover in (1) a first position clear of the archwire slots or (2) a second position overlapping the width and height of the openings in the anterior surfaces of the lugs and completing a continuous archwire tube along the lugs when the closure is in its second position.

2. The self-locking orthodontic bracket of claim 1, wherein the archwire slot includes intersecting inner slot surfaces aligned across the lugs;
the fixed wall extending along the space separating the lugs having an inner surface coextensive and flush with at least one of the inner slot surfaces to extend the archwire slot continuously across the width of the lugs when the cover is in its second position.

3. The self-locking orthodontic bracket of claim 1, wherein the archwire slot includes intersecting inner slot surfaces aligned across the lugs;
the fixed wall extending along the space separating the lugs having an inner surface coextensive and flush with at least one of the inner slot surfaces along the respective lugs to extend the one inner slot surface continuously across the width of the lugs when the cover is in its second position;
the fixed wall being interconnected to the lugs and to the base.

4. The self-locking orthodontic bracket of claim 1, wherein the base includes aligning means for indexing the base in relation to the long tooth axis of a supporting tooth;
the archwire slot being perpendicular to the side surfaces of the lug means and oblique relative to the aligning means of the base for applying a tipping force between an archwire and a supporting tooth.

5. A self-locking orthodontic bracket, comprising:
a base having a posterior surface adapted to be bonded to a tooth;
lug means projecting anteriorly from the base; the lug means including opposed side surfaces;
the lug means further including an anterior surface interrupted by an opening leading to a distally formed archwire slot; and
a closure including a movable cover overlapping the anterior surface, the cover having a width that spans the full width of the lug means and a perpendicular height that is greater than the corresponding height of the opening of the archwire slot across the anterior surface;
the closure further including a pair of guides transversely spaced from one another, the guides slidably engaging the opposed side surfaces of the lug means at location, posterior to the archwire slot for alternately positioning the closure in (1) a first position with the cover clear of the archwire slot or a second position with the cover overlapping the width and height of the opening in the anterior surface of the lug means.

6. The self-locking orthodontic bracket of claim 5, wherein the closure further includes support members interconnecting the cover and the pair of guides.

7. The self-locking orthodontic bracket of claim 5, wherein the closure further includes support members interconnecting the cover and the pair of guides, the support members having inner surfaces that complement the archwire slot to complete a continuous archwire tube that extends along the full width of the lug means when the cover is in its second position.

8. The self-locking orthodontic bracket of claim 5, wherein the base includes aligning means for indexing the base in relation to the long tooth axis of a supporting tooth;
the archwire slot being perpendicular to the side surfaces of the lug means and oblique relative to the aligning means of the base for applying a tipping force between an archwire and a supporting tooth.

9. A self-locking orthodontic bracket, comprising:
a base having a posterior surface adapted to be bonded to a tooth;
lug means projecting anteriorly from the base, the lug means including transversely spaced side surfaces and opposed extensions that project outwardly between the side surfaces;
the lug means further including an anterior surface interrupted by a flush opening leading to a distally formed, transverse archwire slot; and
a closure including a movable cover slidably engaging the anterior surface of the lug means, the cover having a width that spans the full width of the lug means and a perpendicular height that is greater than the corresponding height of the opening of the archwire slot across the anterior surface;
the closure further including a pair of guides transversely spaced from one another, the guides slidably engaging opposed side surfaces of the lug means for alternately positioning the closure means in (1) a first position with the cover clear of the archwire slot or (2) a second position with the cover overlapping the width and height of the opening in the anterior surface of the lug means.

10. The self-locking orthodontic bracket of claim 9, wherein the guides are parallel to the portions of the anterior surface slidably engaged by the cover.

11. The self-locking orthodontic bracket of claim 9, wherein the respective guides engage opposed side surfaces of the lug means which face inwardly toward one another.

12. The self-locking orthodontic bracket of claim 9, wherein the respective guides engage opposed side surfaces of the lug means which face outwardly from one another.

13. The self-locking orthodontic bracket of claim 9, wherein the guides are located posteriorly of the archwire slot.

14. The self-locking orthodontic bracket of claim 9, wherein the base includes aligning means for indexing the base in relation to the long tooth axis of a supporting tooth;

the archwire slot being perpendicular to the side surfaces of the lug means and oblique relative to the aligning means of the base for applying a tipping force between an archwire and a supporting tooth.

15. A self-locking orthodontic bracket, comprising:

a base having a posterior surface adapted to be bonded to a tooth or tooth band;

a pair of tying lugs projecting anteriorly from the base in transversely spaced parallel positions, the tying lugs each including at least one side surface transversely spaced from one another and outwardly projecting extensions;

the tying lugs further including aligned anterior surfaces interrupted by flush openings leading to transversely aligned archwire slots formed distally from the anterior surfaces along the respective tying lugs;

a movable cover overlapping the anterior surfaces of the tying lugs, the cover having a width that spans the full width of the pair of tying lugs and a perpendicular height that is greater than the height of the openings of the archwire slots across the anterior surfaces; and a pair of guides operably supporting the cover and slidably engaging oppositely facing side surfaces on the respective tying lugs for alternately positioning the cover in (1) a first position clear of the archwire slots or (2) a second position overlapping the width and height of the openings in the anterior surfaces of the tying lugs.

16. The self-locking orthodontic bracket of claim 15, wherein the guides engage side surfaces of the respective tying lugs which face inwardly toward one another.

17. The self-locking orthodontic bracket of claim 15, wherein the guides engage side surfaces of the respective tying lugs which face outwardly from one another.

18. The self-locking orthodontic bracket of claim 15, wherein the guides are located posteriorly of the archwire slots.

19. The self-locking orthodontic bracket of claim 15, further comprising:

a pair of support members structurally interconnecting the cover and the pair of guides, the pair of support members being respectively located adjacent corresponding side surfaces of the tying lugs with each support member leading posteriorly from the cover to one of the guides.

20. The self-locking orthodontic bracket of claim 15, wherein the slots formed along the respective tying lugs include slot surfaces aligned across the tying lugs, the bracket further comprising:

a fixed wall extending between the tying lugs, the fixed wall having a surface coextensive and flush with at least a portion of the slot surfaces.

21. The self-locking orthodontic bracket of claim 15, wherein the slots formed along the respective tying lugs include intersecting slot surfaces aligned across the tying lugs, the bracket further comprising:

a fixed wall extending along the space separating the tying lugs, the fixed wall having inner surfaces coextensive and flush with at least one of the inner slot surfaces.

22. The self-locking orthodontic bracket of claim 15, wherein the slots formed along the respective tying lugs include intersecting inner slot surfaces aligned across the tying lugs, the bracket further comprising:

a fixed wall extending along the space separating the tying lugs, the fixed wall having an inner surface coextensive and flush with the inner slot surfaces to extend the archwire slots continuously across the width of the tying lugs when the cover is in its second position.

23. The self-locking orthodontic bracket of claim 15, wherein the slots formed along the respective tying lugs include intersecting inner slot surfaces aligned across the tying lugs, the bracket further comprising:

a fixed wall extending along the space separating the tying lugs, the fixed wall having an inner surface coextensive and flush with one of the inner slot surfaces along the respective lugs to extend the one inner slot surface continuously along the width of the tying lugs when the cover is in its second position.

24. The self-locking orthodontic bracket of claim 15, wherein the slots formed along the respective tying lugs include intersecting inner slot surfaces aligned across the tying lugs, the bracket further comprising:

a fixed wall extending along the space separating the tying lugs, the fixed wall having an inner surface coextensive and flush with one of the inner slot surfaces along the respective lugs to extend the one inner slot surface continuously across the width of the tying lugs when the cover is in its second position;

the fixed wall being interconnected to the tying lugs and to the base.

25. The self-locking orthodontic bracket of claim 15, wherein the slots formed along the respective tying lugs include intersecting slot surfaces aligned across the tying lugs, the bracket further comprising:

a fixed wall extending along the space separating the tying lugs, the fixed wall having an inner surface area that is coextensive and flush with at least one of the slot surfaces; and a support member spanning the space between the pair of tying lugs and structurally interconnecting the cover and guides, the support member including at least one inner surface area that complements the inner surface area of the fixed wall to complete a continuous archwire tube along the tying lugs when the closure is in its second position.

26. The self-locking orthodontic bracket of claim 15 further comprising:
a support member spanning the space between the pair of tying lugs and structurally interconnecting the cover and guides, the support member including an inner surface coextensive and flush with a portion of the aligned archwire slots when the closure is in its second position.

27. The self-locking orthodontic bracket of claim 15, wherein the base includes aligning means for indexing the base in relation to the long tooth axis of a supporting tooth;
the archwire slot being perpendicular to the side surfaces of the tying lug means and oblique relative to the aligning means of the base for applying a tipping force between an archwire and a supporting tooth.

28. A self-locking orthodontic bracket, comprising:
a base having a posterior surface adapted to be bonded to a tooth;
a pair of tying lugs projecting anteriorly from the base in transversely spaced parallel positions, the tying lugs each including a pair of opposed side surfaces transversely spaced from one another and at least one outwardly projecting extension located between the side surfaces;
the tying lugs each including aligned anterior surfaces interrupted by a transverse archwire slot leading distally from the anterior surfaces, the archwire slot having inner slot surfaces that open through the side surfaces of each tying lug;
a movable cover slidably engaging and flush with the anterior surfaces of the tying lugs, the cover Overlapping the full transverse width of the pair of tying lugs and having a perpendicular height that is greater than the height of the archwire slot across the anterior surfaces of the tying lugs;
a pair of guides operably supporting the cover and slidably engaging opposed side surfaces on the respective tying lugs at locations posterior to the archwire slot for alternately positioning the cover in (1) a first position with the cover clear of the archwire slot or (2) a second position with the cover overlapping the width and height of the archwire slot; and
a pair of support members structurally interconnecting the cover and the pair of guides, the pair of support members being respectively located adjacent the opposed side surfaces of the tying lugs engaged by the pair of guides, each support member leading posteriorly from the cover to one of the guides.

29. The self-locking orthodontic bracket of claim 28, further comprising:
a transverse wall integrally joining the pair of tying lugs, the archwire slot being formed continuously across the transverse wall and tying lugs; and
the cover, when in its second position, completing a continuous archwire tube adapted to encircle one or more archwires and extending across the full width of the tying lugs.

30. The self-locking orthodontic bracket of claim 28, further comprising:
a transverse wall including an extension of the anterior surfaces of the tying lugs, the transverse wall integrally joining the pair of tying lugs and the base, the archwire slot being formed continuously along an opening formed in the transverse wall and tying lugs; and
the cover, when in its second position, completing a continuous archwire tube extending across the full width of the tying lugs.

31. The self-locking orthodontic bracket of claim 30, wherein the base includes aligning means for indexing the base in relation to the long tooth axis of a supporting tooth;
the archwire slot being perpendicular to the side surfaces of the tying lug means and oblique relative to the aligning means of the base for applying a tipping force between an archwire and a supporting tooth.

32. A self-locking orthodontic bracket, comprising:
a base having a posterior surface adapted to be bonded to a tooth;
a pair of tying lugs projecting anteriorly from the base in transversely spaced parallel positions, the tying lugs each including first and second side surfaces transversely spaced from one another and opposed outwardly projecting extensions located between the first and second side surfaces;
the tying lugs each including aligned anterior surfaces interrupted by the opening of a transverse archwire, slot leading distally from the anterior surfaces, the archwire slot having an inner slot surface area intersecting the first and second side surfaces of each tying lug;
a transverse wall formed distally the anterior surfaces and extending between the first side surface of the respective lugs, the transverse wall having at least one inner surface formed as a continuation of at least a portion of the transverse archwire slot;
a movable cover slidably engaging and flush with the anterior surfaces of the tying lugs, the cover overlapping the full transverse width of the pair of tying lugs and having a perpendicular height that is greater than the height of the archwire slot across the anterior surfaces of the tying lugs;
a pair of guides operably supporting the cover and slidably engaging the side surfaces on the respective tying lugs at locations posterior to the archwire slot for alternatively positioning the cover in (1) a first position with the cover clear of the archwire slot or (2) a second position with the cover overlapping the width and height of the archwire slot;
support members structurally interconnecting the cover and the pair of guides, the support members spanning the transverse separation between the tying lugs and being configured with at least one inner surface shaped to complete a continuous archwire tube that extends across the full width of the paired tying lugs when the cover is in its second position.

33. The self-locking orthodontic bracket of claim 32 wherein the archwire slot has a rectangular cross-sectional shape formed by a pair of planar side slot surfaces that intersect 1 an anterior slot surface along each tying lug and wherein the surface of the transverse wall formed as a continuation of at least a portion of the transverse archwire slot is aligned with a corresponding side slot surface along each tying lug;
the inner surfaces of the support members being aligned with the remaining side slot surfaces and the anterior slot surfaces along each tying lug when the cover is in its second position.

34. The self-locking orthodontic bracket of claim 32 wherein the archwire slot has a rectangular cross-sectional shape formed by a pair of planar side slot surfaces that intersect an anterior slot surface along each tying lug and wherein the surface of the transverse wall formed as a continuation of at least a portion of the transverse archwire slot is aligned with a corresponding side slot surface along each tying lug;

the support members being two perpendicular elements having intersecting inner surfaces aligned with the remaining side slot surfaces and the anterior slot surfaces of each tying lug when the cover is in its second position.

35. The self-locking orthodontic bracket of claim 32, wherein the base includes aligning means for indexing the base in relation to the long tooth axis of a supporting tooth;

the archwire slot being perpendicular to the side surfaces of the tying lug means and oblique relative to the aligning means of the base for applying a tipping force between an archwire and a supporting tooth.

36. An orthodontic bracket for attachment to a supporting tooth, comprising:

a base having a periphery that intersects a posterior base surface adapted to be bonded to a supporting tooth, the base including aligning means for indexing the base in relation to the long tooth axis of a supporting tooth;

lug means projecting anteriorly frown the base for attachment to an archwire, the lug means including transversely spaced side surfaces;

the lug means further including an anterior surface having a transverse archwire slot formed distally therein, the archwire slot being perpendicular to the side surfaces of the lug means and oblique relative to the aligning means of the base for applying a tipping force between an archwire and a supporting tooth;

a movable cover overlapping the anterior surface of the lug means, the cover having a width that spans the full width of the lug means and a perpendicular height that is greater than the height of the archwire slot across the anterior surface; and guide means slidably supporting the cover on side surfaces of the lug means for alternately positioning the cover in (1) a first position clear of the archwire slot or (2) a second position overlapping the width and height of the archwire slot across the anterior surface of the lug means and completing a continuous archwire tube along the lugs when the closure is in its second position.

37. The orthodontic bracket assembly of claim 36, wherein the periphery of the base is rectangular.

38. The orthodontic bracket assembly of claim 36, wherein the periphery of the base has four planar sides;

the archwire slot across the lug means being oriented at a selected acute angle relative to two sides X of the periphery of the base.

39. The orthodontic bracket assembly of claim 36, wherein the lug means comprises a pair of lugs transversely spaced from one another.

40. The orthodontic bracket assembly of claim 36, wherein the lug means comprises a pair of lugs formed integrally with the base and transversely spaced from one another.

41. The orthodontic bracket assembly of claim 36 wherein the guide means comprises a pair of guides transversely spaced from one another, the guides movably engaging opposed side surfaces of the lug means at locations posterior to the archwire slot.

42. The orthodontic bracket assembly of claim 36 wherein the guide means comprises a pair of guides transversely spaced from one another, the guides movably engaging opposed side surfaces of the lug means facing outwardly from one another, the side surfaces being engaged by the guides at locations posterior to the archwire slot.

43. The orthodontic bracket assembly of claim 36 wherein the guide means comprises a pair of guides parallel to the anterior surface of the cover and transversely spaced from one another, the guides slidably engaging opposed side surfaces of the lug means at locations posterior to the archwire slot.

* * * * *